(12) United States Patent
Iannotti et al.

(10) Patent No.: US 11,730,497 B2
(45) Date of Patent: Aug. 22, 2023

(54) SYSTEM AND METHOD FOR ASSOCIATION OF A GUIDING AID WITH A PATIENT TISSUE

(71) Applicant: THE CLEVELAND CLINIC FOUNDATION, Cleveland, OH (US)

(72) Inventors: Joseph P. Iannotti, Strongsville, OH (US); Wael K. Barsoum, Bay Village, OH (US); Jason A. Bryan, Avon Lake, OH (US); Peter D. O'Neill, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 102 days.

(21) Appl. No.: 15/429,805

(22) Filed: Feb. 10, 2017

(65) Prior Publication Data
US 2017/0150978 A1    Jun. 1, 2017

Related U.S. Application Data

(62) Division of application No. 13/282,509, filed on Oct. 27, 2011, now Pat. No. 9,615,840.
(Continued)

(51) Int. Cl.
*A61B 17/17* (2006.01)
*A61B 34/10* (2016.01)
(Continued)

(52) U.S. Cl.
CPC ........ *A61B 17/1778* (2016.11); *A61B 17/151* (2013.01); *A61B 17/1746* (2013.01);
(Continued)

(58) Field of Classification Search
CPC ............ A61B 17/1742; A61B 17/1746; A61B 17/1739; A61B 17/1778; A61B 17/151;
(Continued)

(56) References Cited

U.S. PATENT DOCUMENTS

| 4,841,975 A | 6/1989 | Woolson |
| 5,030,219 A | 7/1991 | Matsen et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

U.S. Appl. No. 61/373,092 (Year: 2010).*
(Continued)

*Primary Examiner* — Marcela I. Shirsat
(74) *Attorney, Agent, or Firm* — Norton Rose Fulbright Canada LLP

(57) ABSTRACT

A patient tissue includes a primary patient tissue area and an anatomically differentiated bordering secondary patient tissue area. An apparatus is at least partially customized responsive to preoperative imaging of the patient tissue. Means are provided for mating with the primary patient tissue area in a preselected relative orientation. Means are provided for fixing a first landmark to the primary patient tissue area in at least one of a predetermined marking location and a predetermined marking trajectory. Means are provided for fixing a second landmark to the secondary patient tissue area in at least one of a predetermined marking location and a predetermined marking trajectory. A method of associating a plurality of landmarks with a patient tissue is also provided.

20 Claims, 18 Drawing Sheets

Related U.S. Application Data

(60) Provisional application No. 61/408,359, filed on Oct. 29, 2010.

(51) Int. Cl.
*A61B 17/15* (2006.01)
*A61B 17/56* (2006.01)

(52) U.S. Cl.
CPC ............ *A61B 34/10* (2016.02); *A61B 17/152* (2013.01); *A61B 2017/568* (2013.01); *A61B 2034/104* (2016.02); *A61B 2034/105* (2016.02); *A61B 2034/108* (2016.02)

(58) Field of Classification Search
CPC .......... A61B 17/152; A61B 2017/1778; A61B 2034/104
USPC ..................... 606/86 r, 87, 80, 96, 102, 104; 623/19.11–19.14
See application file for complete search history.

(56) References Cited

U.S. PATENT DOCUMENTS

| | | | |
|---|---|---|---|
| 5,098,383 A | 3/1992 | Hemmy et al. |
| 5,490,854 A | 2/1996 | Fisher et al. |
| 5,768,134 A | 6/1998 | Swaelens et al. |
| 5,769,856 A | 6/1998 | Dong et al. |
| 5,871,018 A | 2/1999 | Delp et al. |
| 5,916,219 A | 6/1999 | Matsuno et al. |
| 6,327,491 B1 | 12/2001 | Franklin et al. |
| 6,364,910 B1 | 4/2002 | Shultz et al. |
| 6,712,856 B1 | 3/2004 | Carignan et al. |
| 6,772,026 B2 | 8/2004 | Bradbury et al. |
| 7,194,120 B2 | 3/2007 | Wicker et al. |
| 7,357,057 B2 | 4/2008 | Chiang |
| 7,468,075 B2 | 12/2008 | Lang et al. |
| 7,510,557 B1 | 3/2009 | Bonutti |
| 7,534,263 B2 | 5/2009 | Burdulis |
| 7,618,451 B2 | 11/2009 | Berez et al. |
| 7,634,119 B2 | 12/2009 | Tsougarakis et al. |
| 7,717,956 B2 | 5/2010 | Lang |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,806,897 B1 | 10/2010 | Bonutti |
| 7,967,868 B2 | 6/2011 | White et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,077,950 B2 | 12/2011 | Tsougarakis et al. |
| 8,083,745 B2 | 12/2011 | Lang et al. |
| 8,092,465 B2 | 1/2012 | Metzger et al. |
| 8,094,900 B2 | 1/2012 | Steines et al. |
| 8,105,330 B2 | 1/2012 | Fitz et al. |
| 8,122,582 B2 | 2/2012 | Burdulis, Jr. et al. |
| 8,133,234 B2 | 3/2012 | Meridew et al. |
| 8,160,345 B2 | 4/2012 | Pavlovskaia et al. |
| 8,175,683 B2 | 5/2012 | Roose |
| 8,221,430 B2 | 7/2012 | Park et al. |
| 8,234,097 B2 | 7/2012 | Steines et al. |
| 8,241,293 B2 | 8/2012 | Stone et al. |
| 8,282,646 B2 | 10/2012 | Schoenefeld et al. |
| 8,298,237 B2 | 10/2012 | Schoenefeld |
| 8,337,501 B2 | 12/2012 | Fitz et al. |
| 8,337,507 B2 | 12/2012 | Lang et al. |
| 8,343,218 B2 | 1/2013 | Lang et al. |
| 8,366,771 B2 | 2/2013 | Burdulis et al. |
| 8,377,129 B2 | 2/2013 | Fitz et al. |
| 8,439,926 B2 | 5/2013 | Bojarski et al. |
| 8,460,304 B2 | 6/2013 | Fitz et al. |
| 8,480,754 B2 | 7/2013 | Bojarski et al. |
| 8,500,740 B2 | 8/2013 | Bojarski et al. |
| 8,529,568 B2 | 9/2013 | Bouadi |
| 8,529,630 B2 | 9/2013 | Bojarski |
| 8,585,708 B2 | 9/2013 | Fitz et al. |
| 8,545,569 B2 | 10/2013 | Fitz et al. |
| 8,551,099 B2 | 10/2013 | Lang |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,556,971 B2 | 10/2013 | Lang |
| 8,556,983 B2 | 10/2013 | Bojarski et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,617,172 B2 | 12/2013 | Fitz et al. |
| 8,617,242 B2 | 12/2013 | Philipp |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Fitz et al. |
| 8,682,052 B2 | 3/2014 | Fitz et al. |
| 8,882,770 B2 | 11/2014 | Barsoum |
| 9,254,155 B2 | 2/2016 | Iannotti |
| 9,693,878 B2 * | 7/2017 | Kunz ................. A61B 17/1746 |
| 9,717,508 B2 | 8/2017 | Iannotti |
| 2003/0055502 A1 | 3/2003 | Lang et al. |
| 2003/0216669 A1 | 11/2003 | Lang et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2005/0107799 A1 | 5/2005 | Graf |
| 2005/0148843 A1 | 7/2005 | Roose |
| 2005/0234461 A1 | 10/2005 | Burdulis et al. |
| 2005/0267584 A1 | 12/2005 | Burdulis et al. |
| 2006/0079963 A1 * | 4/2006 | Hansen ..................... A61F 2/40 |
| | | | 623/19.11 |
| 2006/0111722 A1 | 5/2006 | Bouadi |
| 2007/0083266 A1 | 4/2007 | Lang |
| 2007/0100462 A1 | 5/2007 | Lang et al. |
| 2007/0156171 A1 | 7/2007 | Lang et al. |
| 2007/0157783 A1 | 7/2007 | Chiang |
| 2007/0173815 A1 | 7/2007 | Murase |
| 2007/0198022 A1 | 8/2007 | Lang et al. |
| 2007/0226986 A1 | 10/2007 | Park et al. |
| 2007/0233141 A1 | 10/2007 | Park et al. |
| 2007/0233269 A1 | 10/2007 | Steines et al. |
| 2007/0250169 A1 | 10/2007 | Lang |
| 2007/0288030 A1 | 12/2007 | Metzger et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0195216 A1 | 8/2008 | Philipp |
| 2008/0215059 A1 | 9/2008 | Carignan et al. |
| 2008/0243127 A1 | 10/2008 | Lang et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0319491 A1 | 12/2008 | Schoenefeld |
| 2009/0018546 A1 | 1/2009 | Daley |
| 2009/0024131 A1 | 1/2009 | Metzgu et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram |
| 2009/0093816 A1 | 4/2009 | Roose et al. |

(56) References Cited

U.S. PATENT DOCUMENTS

| | | |
|---|---|---|
| 2009/0099567 A1 | 4/2009 | Zajac |
| 2009/0110498 A1 | 4/2009 | Park et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0157083 A1 | 6/2009 | Park et al. |
| 2009/0163922 A1 | 6/2009 | Meridew et al. |
| 2009/0222014 A1 | 9/2009 | Bojarksi et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228113 A1 | 9/2009 | Lang et al. |
| 2009/0254093 A1 | 10/2009 | White et al. |
| 2009/0270868 A1 | 10/2009 | Park et al. |
| 2009/0276045 A1 | 11/2009 | Lang |
| 2009/0306676 A1 | 12/2009 | Lang et al. |
| 2009/0307893 A1 | 12/2009 | Burdulis, Jr. et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0082035 A1* | 4/2010 | Keefer ............... A61B 17/1746 606/91 |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0256479 A1 | 10/2010 | Park et al. |
| 2010/0262150 A1 | 10/2010 | Lian |
| 2010/0274253 A1 | 10/2010 | Ure |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0190775 A1* | 8/2011 | Ure ........................ A61F 2/4609 606/91 |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1 | 9/2011 | White et al. |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109137 A1 | 5/2012 | Iannotti |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123420 A1* | 5/2012 | Honiball ............ A61B 17/1764 606/87 |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |

(56) References Cited

U.S. PATENT DOCUMENTS

| | | | |
|---|---|---|---|
| 2012/0271366 A1 | 10/2012 | Katrana et al. | |
| 2012/0276509 A1 | 11/2012 | Iannotti | |
| 2012/0277751 A1 | 11/2012 | Catanzarite et al. | |
| 2012/0289966 A1 | 11/2012 | Fitz et al. | |
| 2012/0296337 A1 | 11/2012 | Fitz et al. | |
| 2013/0018379 A1 | 1/2013 | Fitz et al. | |
| 2013/0018380 A1 | 1/2013 | Fitz et al. | |
| 2013/0018464 A1 | 1/2013 | Fitz et al. | |
| 2013/0023884 A1 | 1/2013 | Fitz et al. | |
| 2013/0024000 A1 | 1/2013 | Bojarski et al. | |
| 2013/0030419 A1 | 1/2013 | Fitz et al. | |
| 2013/0030441 A1 | 1/2013 | Fitz et al. | |
| 2013/0079781 A1 | 3/2013 | Fitz et al. | |
| 2013/0079876 A1 | 3/2013 | Fitz et al. | |
| 2013/0081247 A1 | 4/2013 | Fitz et al. | |
| 2013/0096562 A1 | 4/2013 | Fitz et al. | |
| 2013/0103363 A1 | 4/2013 | Lang et al. | |
| 2013/0110471 A1 | 5/2013 | Lang et al. | |
| 2013/0123792 A1 | 5/2013 | Fitz et al. | |
| 2013/0184713 A1 | 7/2013 | Bojarski et al. | |
| 2013/0197870 A1 | 8/2013 | Steines et al. | |
| 2013/0211409 A1 | 8/2013 | Burdulis, Jr. et al. | |
| 2013/0211410 A1 | 8/2013 | Landes et al. | |
| 2013/0211531 A1 | 8/2013 | Steines et al. | |
| 2013/0245803 A1 | 9/2013 | Lang | |
| 2013/0253522 A1 | 9/2013 | Bojarski et al. | |
| 2013/0289570 A1 | 10/2013 | Chao | |
| 2013/0296874 A1 | 11/2013 | Chao | |
| 2013/0297031 A1 | 11/2013 | Hafez | |
| 2013/0317511 A1 | 11/2013 | Bojarski et al. | |
| 2013/0331850 A1 | 12/2013 | Bojarski et al. | |
| 2014/0005792 A1 | 1/2014 | Lang et al. | |
| 2014/0012266 A1* | 1/2014 | Bonin, Jr. | A61B 17/15 606/88 |
| 2014/0029814 A1 | 1/2014 | Fitz et al. | |
| 2014/0031826 A1 | 1/2014 | Bojarski et al. | |
| 2014/0039631 A1 | 2/2014 | Bojarski et al. | |
| 2014/0058396 A1 | 2/2014 | Fitz et al. | |
| 2014/0058397 A1 | 2/2014 | Fitz et al. | |
| 2014/0066935 A1 | 3/2014 | Fitz et al. | |
| 2014/0066936 A1 | 3/2014 | Fitz et al. | |
| 2014/0074441 A1 | 3/2014 | Fitz et al. | |
| 2014/0081342 A1 | 3/2014 | Iannotti | |
| 2014/0086780 A1 | 3/2014 | Miller et al. | |
| 2016/0095608 A1 | 4/2016 | Iannotti | |
| 2017/0071647 A1 | 3/2017 | Iannotti | |
| 2017/0296205 A1 | 10/2017 | Iannotti | |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 1729483 B | 10/2013 |
| CN | 103476363 A | 12/2013 |
| DE | 60336002 D1 | 3/2011 |
| DE | 60239674 D1 | 5/2011 |
| DE | 602004032166 D1 | 5/2011 |
| DE | 602005027391 D1 | 5/2011 |
| EP | 0558789 A1 | 9/1993 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1639949 A1 | 3/2006 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |

(56) References Cited

FOREIGN PATENT DOCUMENTS

| | | |
|---|---|---|
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 0001316 A1 | 1/2000 |
| WO | 2001/070142 A1 | 9/2001 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009058319 A1 | 5/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | WO-2010150223 A1 * | 12/2010 ........... A61B 17/175 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Taylor et al, "Computer-Integrated Surgery, Technology and Clinical Applications", The MIT Press, Cambridge, MA, London, UK, pp. 451-463.

Hofmann et al, "Natural-Knee II System", Intermedics Orthopedics, Austin, TX, 1995.

Murase et al., "Three-Dimensional Corrective Osteotomy of Malunited Fractures of the Upper Extremity with Use of a Computer Simulation System", J Bone Joint Surg Am., 90:.2375-2389 (2008).

Oka et al., "Accuracy of Corrective Osteotomy Using a Custom-Designed Device Based on a Novel Computer Simulation System", J Orthop Sci, 16:85-92 (2011).

* cited by examiner

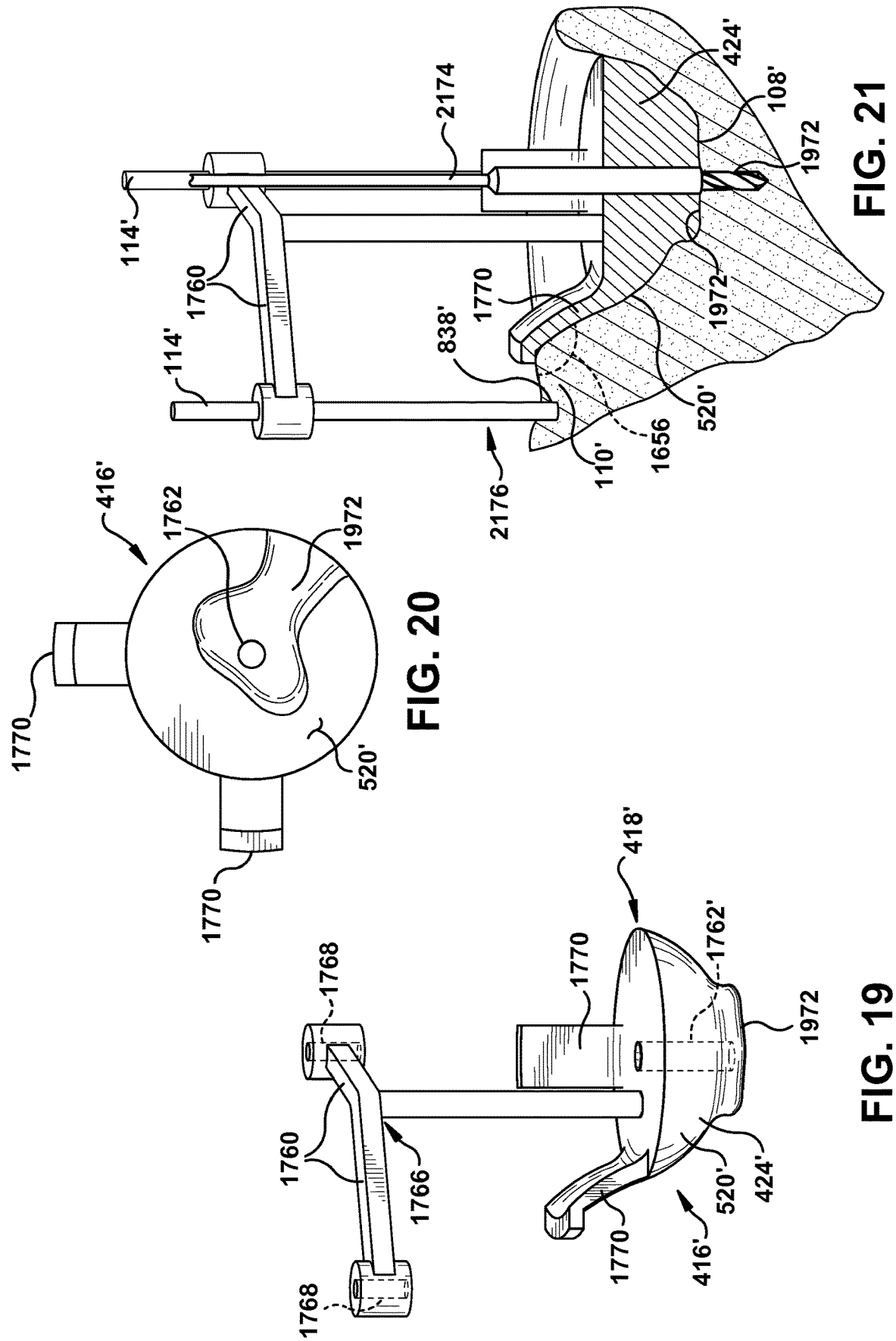

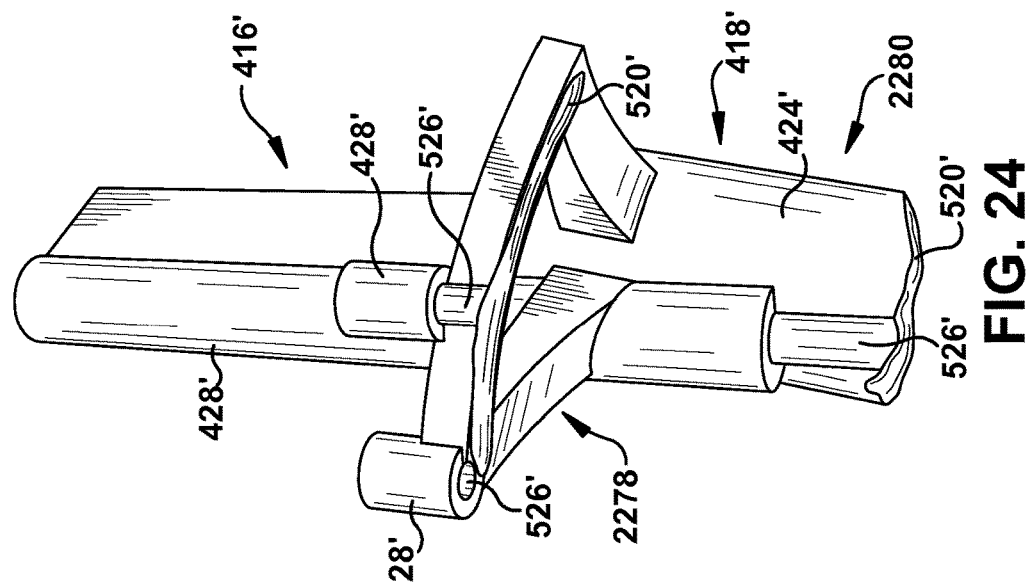
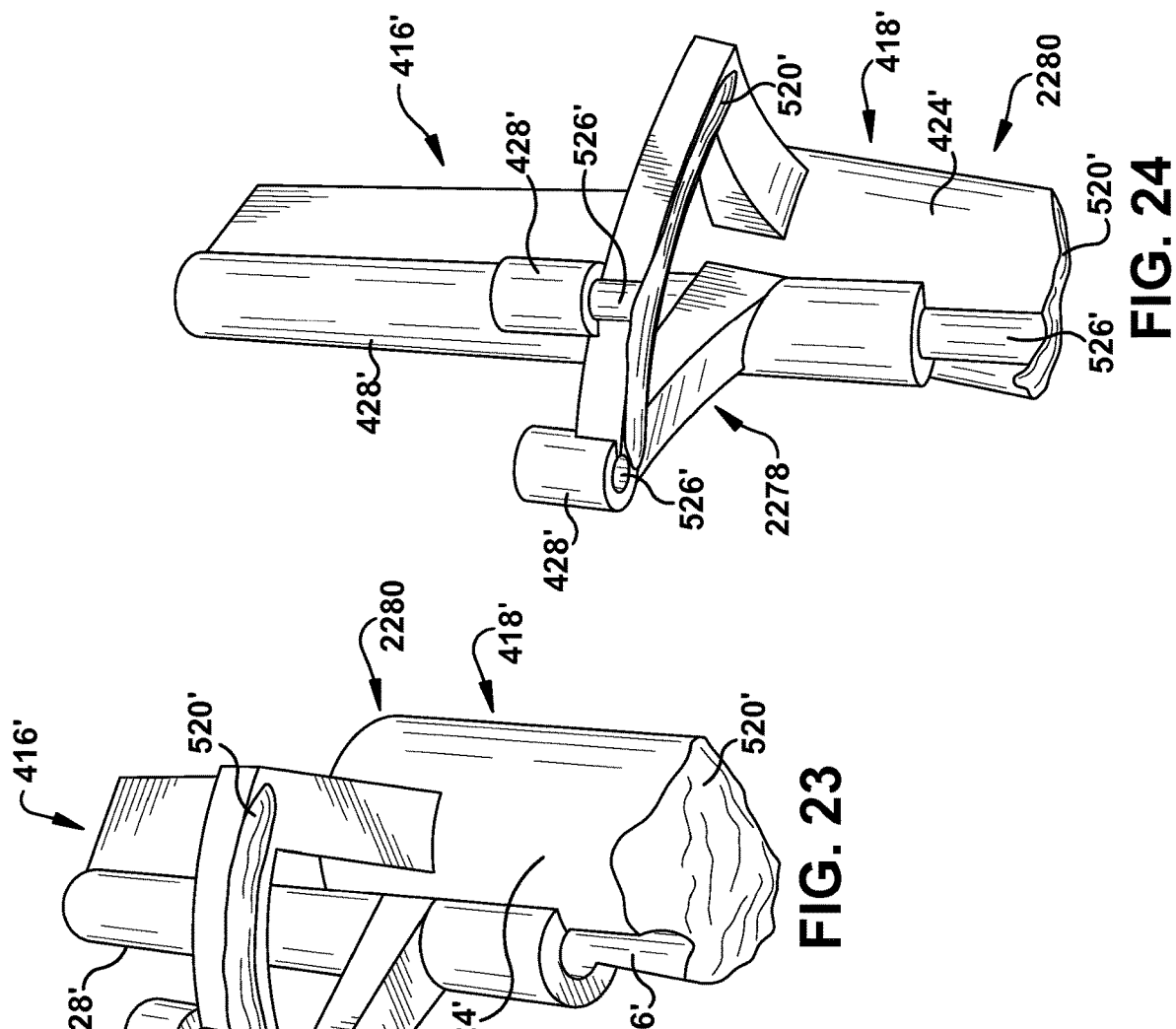
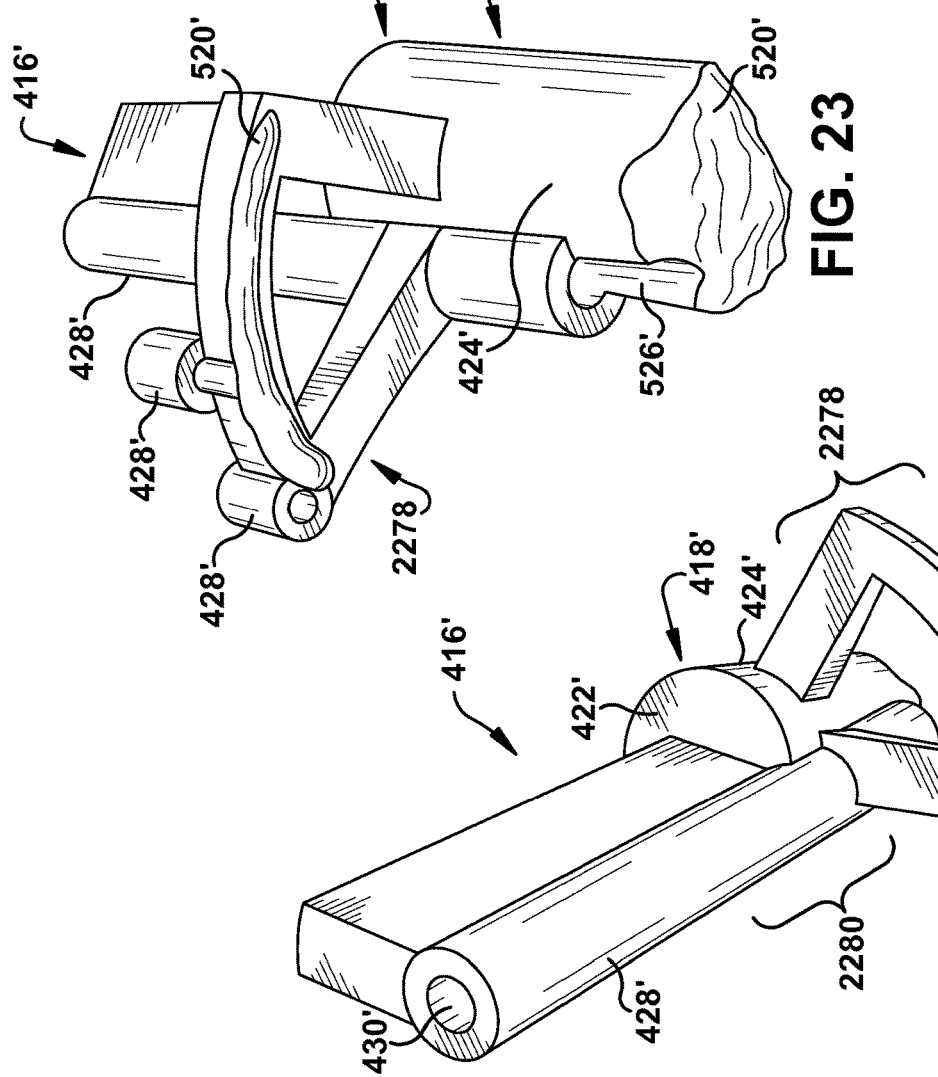

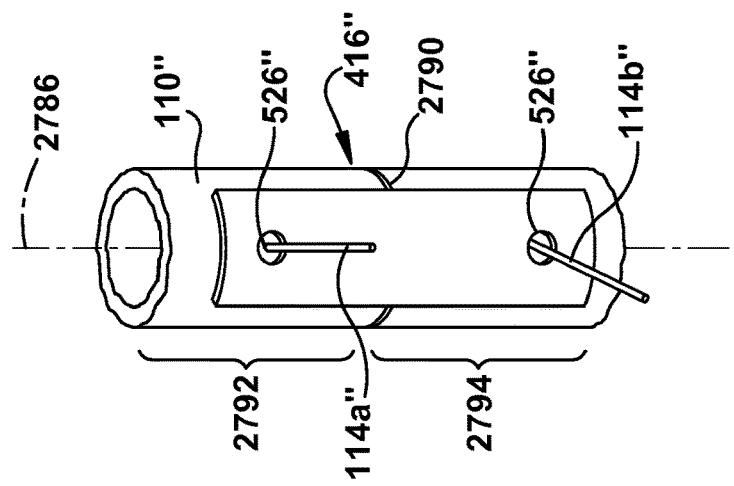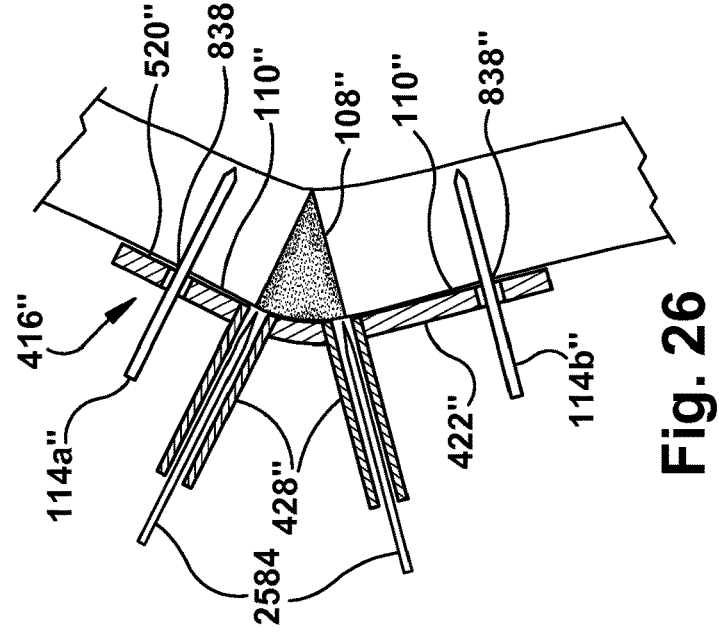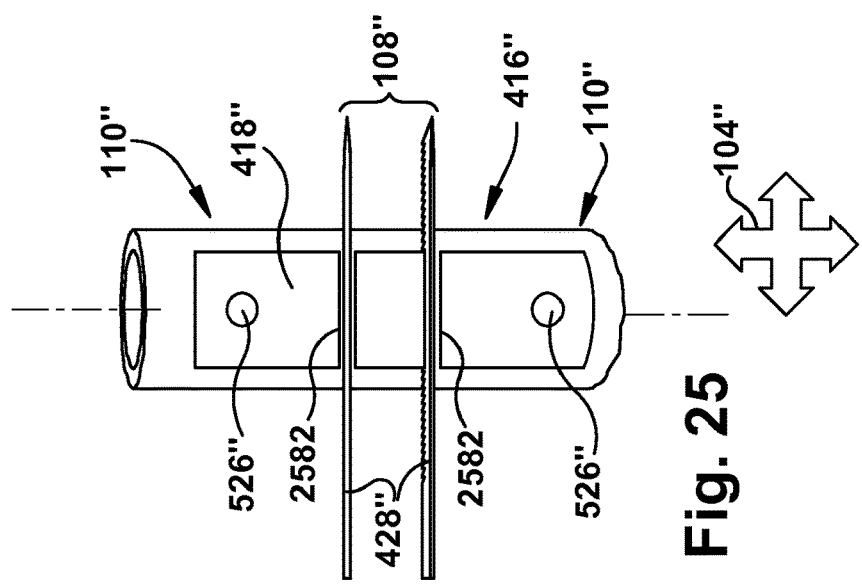

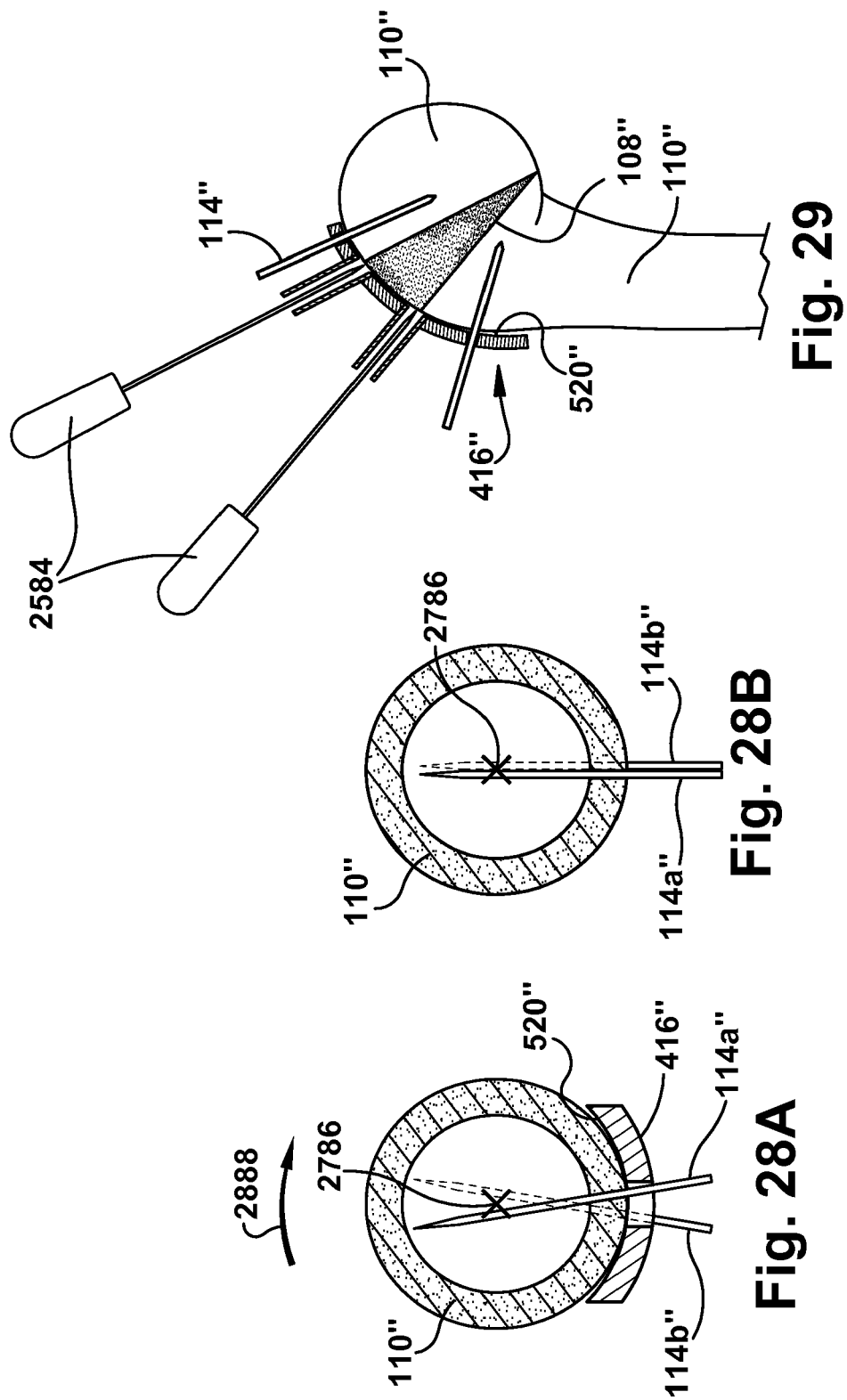

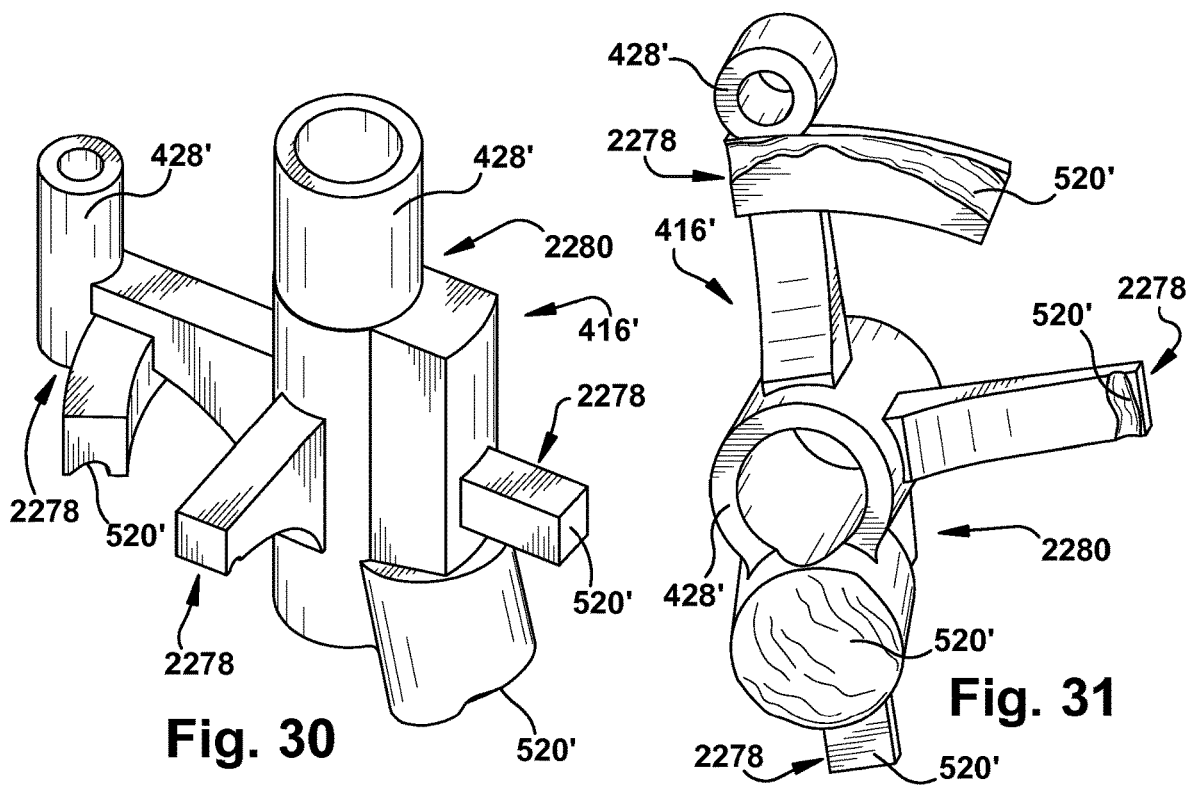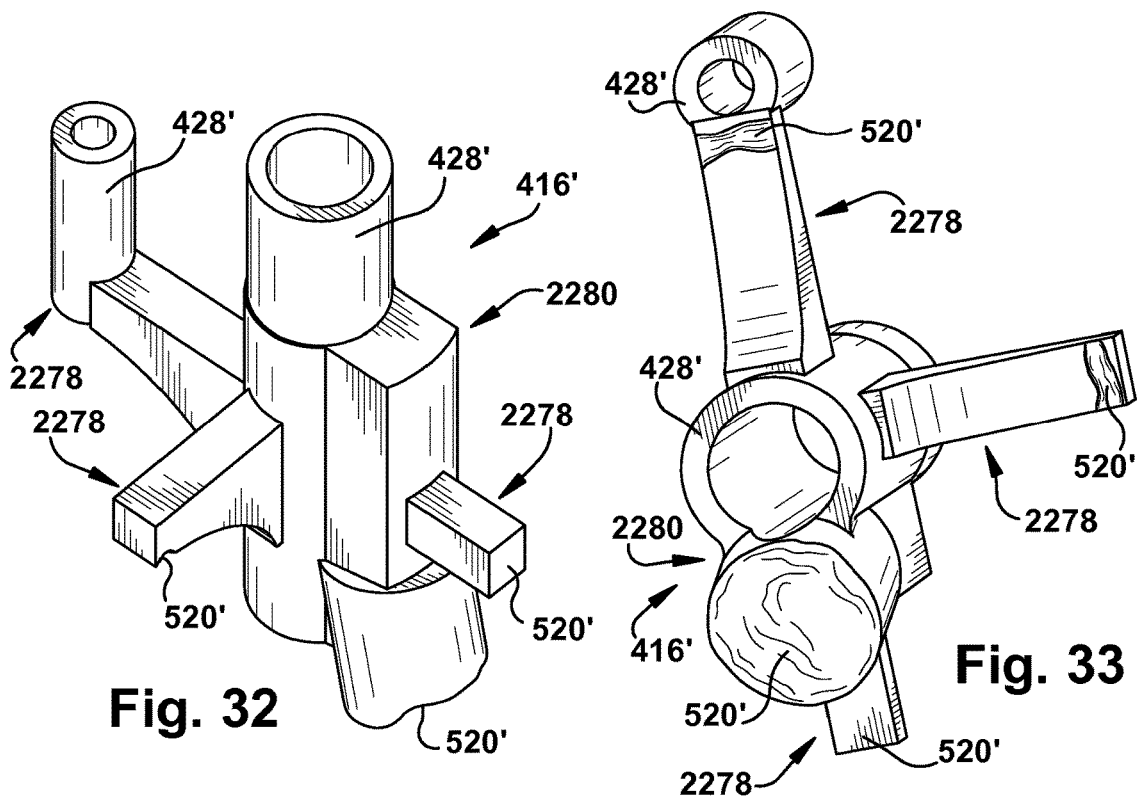

SYSTEM AND METHOD FOR ASSOCIATION OF A GUIDING AID WITH A PATIENT TISSUE

CROSS-REFERENCE TO RELATED APPLICATION

This application is a divisional of U.S. Non-Provisional application Ser. No. 13/282,509, filed on Oct. 27, 2011 which claims priority from U.S. Provisional Application No. 61/408,359, filed Oct. 29, 2010, the subject matter of which is incorporated herein by reference in its entirety.

TECHNICAL FIELD

The present invention relates to a system and method for association of a guiding aid with a patient tissue and, more particularly, to a system and method for associating at least one landmark with the patient tissue for assisting with attachment of a stock prosthetic implant to the patient tissue.

BACKGROUND OF THE INVENTION

In the installation of a prosthetic shoulder joint into a patient's body, a glenoid component is implanted into the glenoid vault of the patient's scapula. An obverse surface of the glenoid component is configured for articulating contact with a humeral component carried by the patient's humerus. A reverse surface of the glenoid component is secured to the bone surface of the glenoid vault.

Because the shoulder prosthesis is normally provided to correct a congenital or acquired defect of the native shoulder joint, the glenoid vault often exhibits a pathologic, nonstandard anatomic configuration. A surgeon must compensate for such pathologic glenoid vault anatomy when implanting the glenoid component in striving to achieve a solid anchoring of the glenoid component into the glenoid vault. Detailed preoperative planning, using two- or three-dimensional internal images of the shoulder joint, often assists the surgeon in compensating for the patient's anatomical limitations. During the surgery, an elongated pin may be inserted into the surface of the patient's bone, at a predetermined trajectory and location, to act as a passive landmark or active guiding structure in carrying out the preoperatively planned implantation. This "guide pin" may remain as a portion of the implanted prosthetic joint or may be removed before the surgery is concluded. This type of pin-guided installation is common in any joint replacement procedure—indeed, in any type of surgical procedure in which a surgeon-placed fixed landmark is desirable.

In addition, and again in any type of surgical procedure, modern minimally invasive surgical techniques may dictate that only a small portion of the bone or other tissue surface being operated upon is visible to the surgeon. Depending upon the patient's particular anatomy, the surgeon may not be able to precisely determine the location of the exposed area relative to the remaining, obscured portions of the bone through mere visual observation. Again, a guide pin may be temporarily or permanently placed into the exposed bone surface to help orient the surgeon and thereby enhance the accuracy and efficiency of the surgical procedure.

A carefully placed guide pin or other landmark, regardless of the reason provided, will reduce the need for intraoperative imaging in most surgical procedures and should result in decreased operative time and increased positional accuracy, all of which are desirable in striving toward a positive patient outcome.

SUMMARY OF THE INVENTION

In an embodiment of the present invention, an apparatus for associating a plurality of landmarks with a patient tissue is described. The patient tissue includes a primary patient tissue area and an anatomically differentiated bordering secondary patient tissue area. The apparatus is at least partially customized responsive to preoperative imaging of the patient tissue. Means are provided for mating with the primary patient tissue area in a preselected relative orientation. Means are provided for fixing a first landmark to the primary patient tissue area in at least one of a predetermined marking location and a predetermined marking trajectory. Means are provided for fixing a second landmark to the secondary patient tissue area in at least one of a predetermined marking location and a predetermined marking trajectory.

In an embodiment of the present invention, an apparatus for associating a plurality of landmarks with a patient tissue is described. Each landmark is associated with the patient tissue in at least one of a predetermined marking location and a predetermined marking trajectory. The patient tissue includes a primary patient tissue area and an anatomically differentiated bordering secondary patient tissue area. The apparatus is at least partially customized responsive to preoperative imaging of the patient tissue. A base has a lower base surface contoured to mate with both the primary and secondary patient tissue areas in a preselected relative orientation. The lower base surface is spaced apart from an upper base surface by a base body. A plurality of base apertures extend between the upper and lower base surfaces through the base body. A plurality of guiding bosses protrude from the base. Each guiding boss has a guiding bore extending therethrough. Each guiding bore extends collinearly with a corresponding base aperture to permit insertion of a landmark through the apparatus. Each guiding bore and corresponding base aperture cooperatively define at least one of the predetermined marking location and the predetermined marking trajectory for the landmark. At least one landmark is guided by the apparatus into engagement with a marking location in the primary patient tissue area and at least one landmark is guided by the apparatus into engagement with a marking location in the secondary patient tissue area.

In an embodiment of the present invention, an apparatus for associating a plurality of landmarks with a patient tissue is described. Each landmark is associated with the patient tissue in at least one of a predetermined marking location and a predetermined marking trajectory. The patient tissue includes a primary patient tissue area and an anatomically differentiated bordering secondary patient tissue area. The apparatus is at least partially customized responsive to preoperative imaging of the patient tissue. A base has a lower base surface contoured to mate with the primary patient tissue area in a preselected relative orientation. The lower base surface is spaced apart from an upper base surface by a base body. A stem has longitudinally separated first and second stem ends. The first stem end is attached directly to the base and the stem extends upward from the base. At least one spacing arm is attached directly to the second stem end. Each spacing arm is longitudinally spaced from the base and has an arm guide aperture laterally spaced from the stem. The arm guide aperture is configured to guide placement of a landmark inserted at least partially therethrough in at least one of the predetermined marking location and the predetermined marking trajectory. The marking location is in the secondary patient tissue area.

In an embodiment of the present invention, a method of associating a plurality of landmarks with a patient tissue is described. Each landmark is associated with the patient tissue in at least one of a predetermined marking location and a predetermined marking trajectory. The patient tissue includes a primary patient tissue area and an anatomically differentiated bordering secondary patient tissue area. A landmark guide having a base at least partially customized responsive to preoperative imaging of the patient tissue is provided. The base has a lower base surface contoured to mate with the primary patient tissue area in a preselected relative orientation. The base of the landmark guide is mated with the primary patient tissue area in a preselected relative orientation. A first landmark is fixed to the primary patient tissue area in at least one of the predetermined marking location and the predetermined marking trajectory. A second landmark is fixed to the secondary patient tissue area in at least one of the predetermined marking location and the predetermined marking trajectory.

In an embodiment of the present invention, an apparatus for associating a plurality of landmarks with a patient tissue is described. Each landmark is associated with the patient tissue in at least one of a predetermined marking location and a predetermined marking trajectory. The removal of a predetermined amount of resection patient tissue and rearrangement of a remaining patient tissue is guided. The apparatus is at least partially customized responsive to preoperative imaging of the patient tissue. A first guide is configured to contact the resection patient tissue and the remaining patient tissue and to guide surgical contact with the patient tissue. A first guide base has a lower first guide base surface contoured to mate with both the resection and remaining patient tissues in a preselected relative orientation. The lower first guide base surface is spaced apart from an upper first guide base surface by a first guide base body. At least one first guide landmark guiding aperture extends between the upper and lower first guide base surfaces through the first guide base body to permit insertion of at least one landmark therethrough. A plurality of first guide cutting guide apertures extend between the upper and lower first guide base surfaces through the first guide base body to permit penetration of at least one cutting tool through the first guide. At least one of the first guide landmark guiding apertures defines at least one of the predetermined marking location and the predetermined marking trajectory for a first landmark and a plurality of the first guide cutting guide apertures each defines at least one cutting plane location and orientation for a cutting tool to make at least one resection cut into the patient tissue. The first guide is configured to cut the resection patient tissue for removal from the remaining patient tissue.

BRIEF DESCRIPTION OF THE DRAWINGS

For a better understanding of the invention, reference may be made to the accompanying drawings, in which:

FIG. 19 is a side view of the embodiment of FIG. 17 in a second configuration;

FIG. 20 is a partial bottom view of the embodiment of FIG. 19;

FIG. 21 is a schematic side view of the embodiment of FIG. 19 in the use environment of FIG. 16;

FIG. 22 is a perspective top view of the embodiment of FIG. 17 in a third configuration;

FIG. 23 is a perspective bottom view of the embodiment of FIG. 22;

FIG. 24 is a perspective side view of the embodiment of FIG. 22;

FIG. 25 is a front view of an embodiment of the present invention in a third example use environment;

FIG. 26 is a schematic side view of the embodiment of FIG. 25;

FIG. 27 is a front view of the embodiment of FIG. 25 in a second configuration;

FIGS. 28A-28B depict an example use sequence of the second configuration of FIG. 27;

FIG. 29 is a schematic side view of the embodiment of FIG. 25 in a third configuration and in a fourth example use environment FIG. 30 is a perspective top view of the embodiment of FIG. 17 in a fourth configuration;

FIG. 31 is a perspective bottom view of the embodiment of FIG. 30;

FIG. 32 is a perspective top view of the embodiment of FIG. 17 in a fifth configuration;

FIG. 33 is a perspective bottom view of the embodiment of FIG. 32;

DESCRIPTION OF EMBODIMENTS

The patient tissue is shown and described herein at least as a scapula or a pelvis and the prosthetic implant component is shown and described herein at least as a glenoid prosthetic shoulder component or an acetabular prosthetic hip component, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention.

Figure 1:
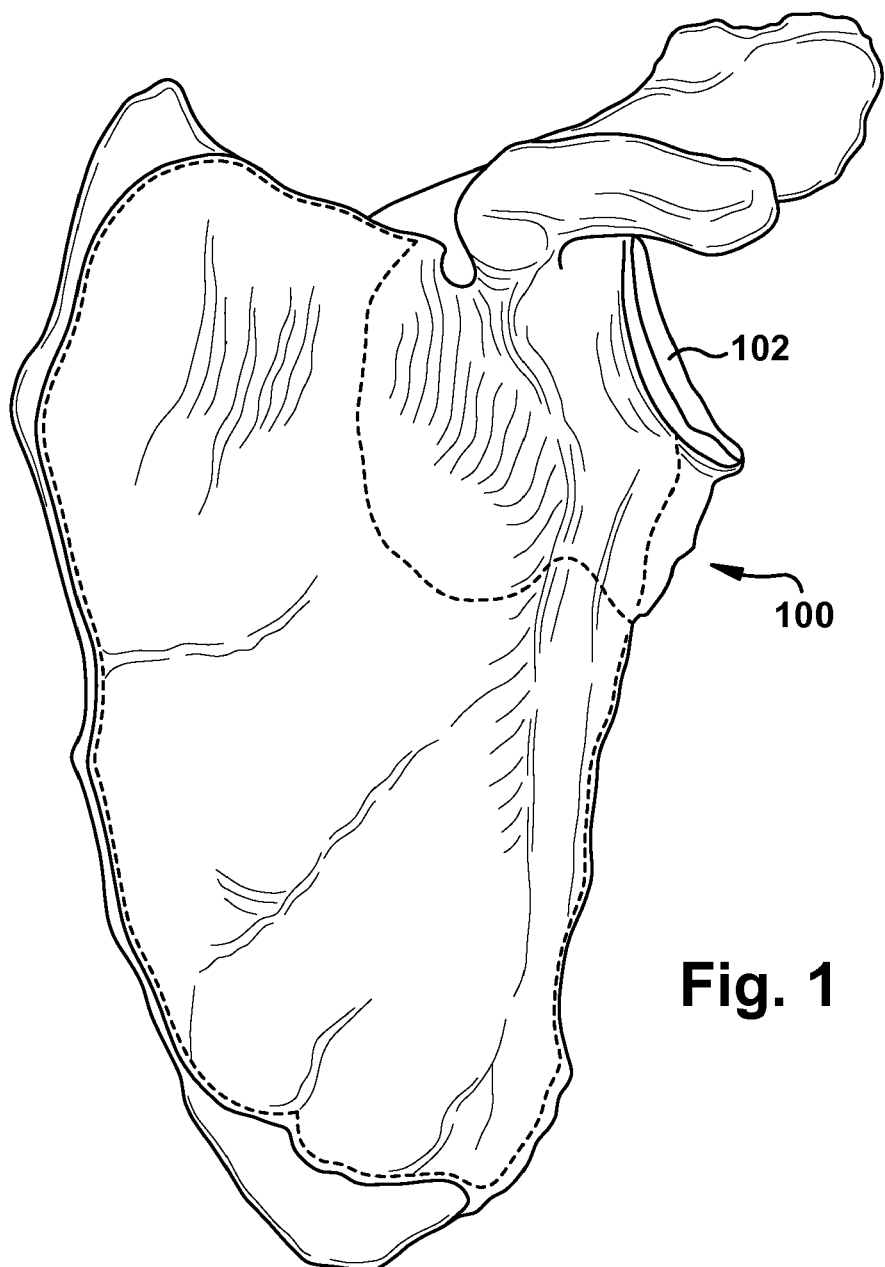
FIG. 1 is a side view of a first example use environment.

FIG. 1 depicts a portion of the external surface of a (left) scapula 100, viewed from the anterior direction toward the posterior direction, which is an example of a possible patient tissue use environment for the described systems, apparatuses, and methods. The humerus (not shown) of a patient attaches to the scapula 100 at the glenoid fossa 102 to form the ball-and-socket shoulder joint.

Figure 2:
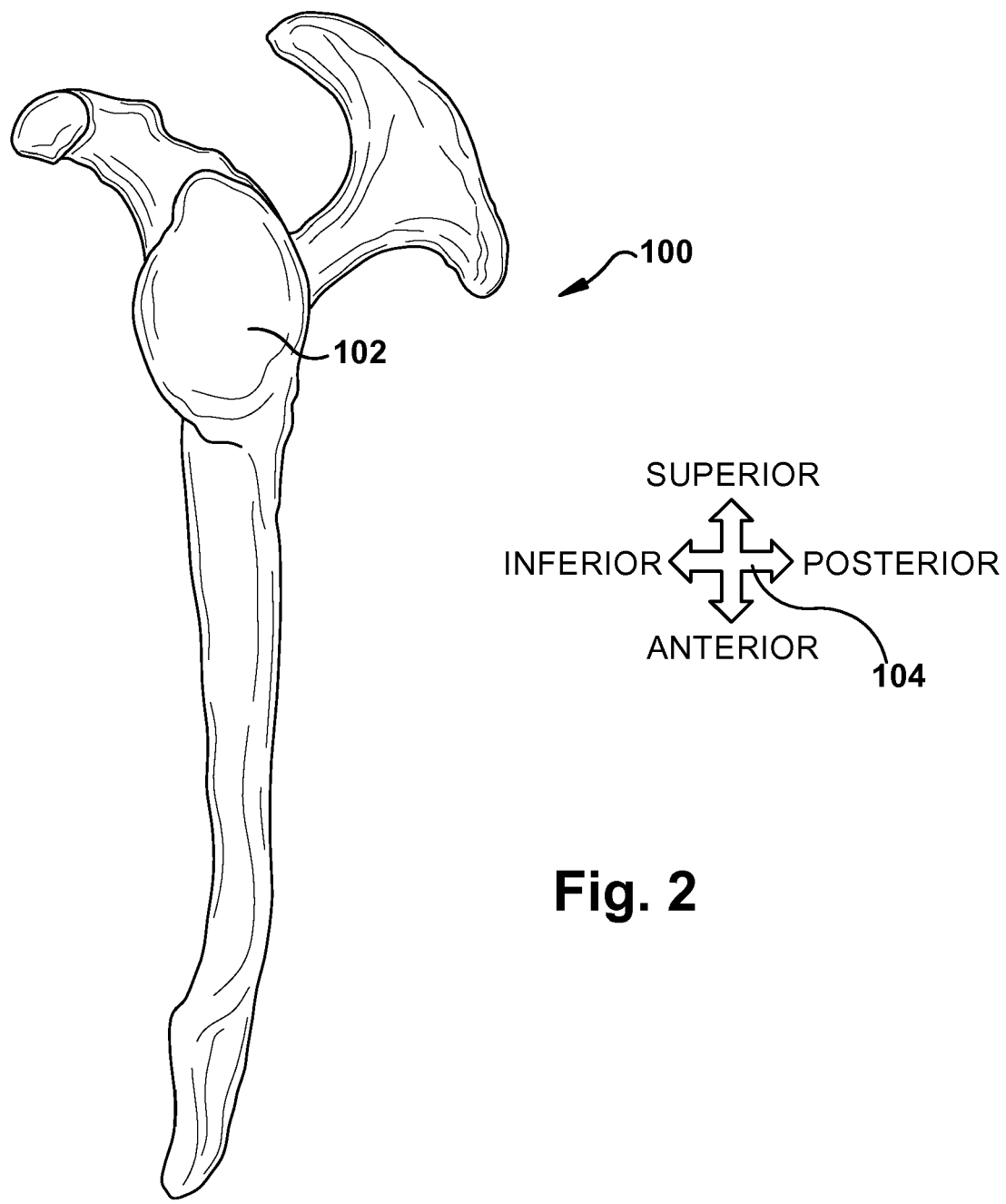
FIG. 2 is a front view of the example use environment of FIG. 1.

The glenoid fossa 102 is shown in greater detail in FIG. 2, a view taken orthogonally from FIG. 1. The term "lateral" is used herein to refer to a direction which, in FIG. 2, lies substantially within the plane of the drawing as shown by directional arrow 104 and includes all of the superior, inferior, anterior, and posterior directions. The term "longitudinal" is used herein to refer to a direction defined perpendicular to the plane created by directional arrow 104, with the longitudinal direction being substantially into and out of the plane of the drawing in FIG. 2 and representing the proximal (toward the medial plane of the body) and distal (out from the body) directions, respectively.

Figure 3:
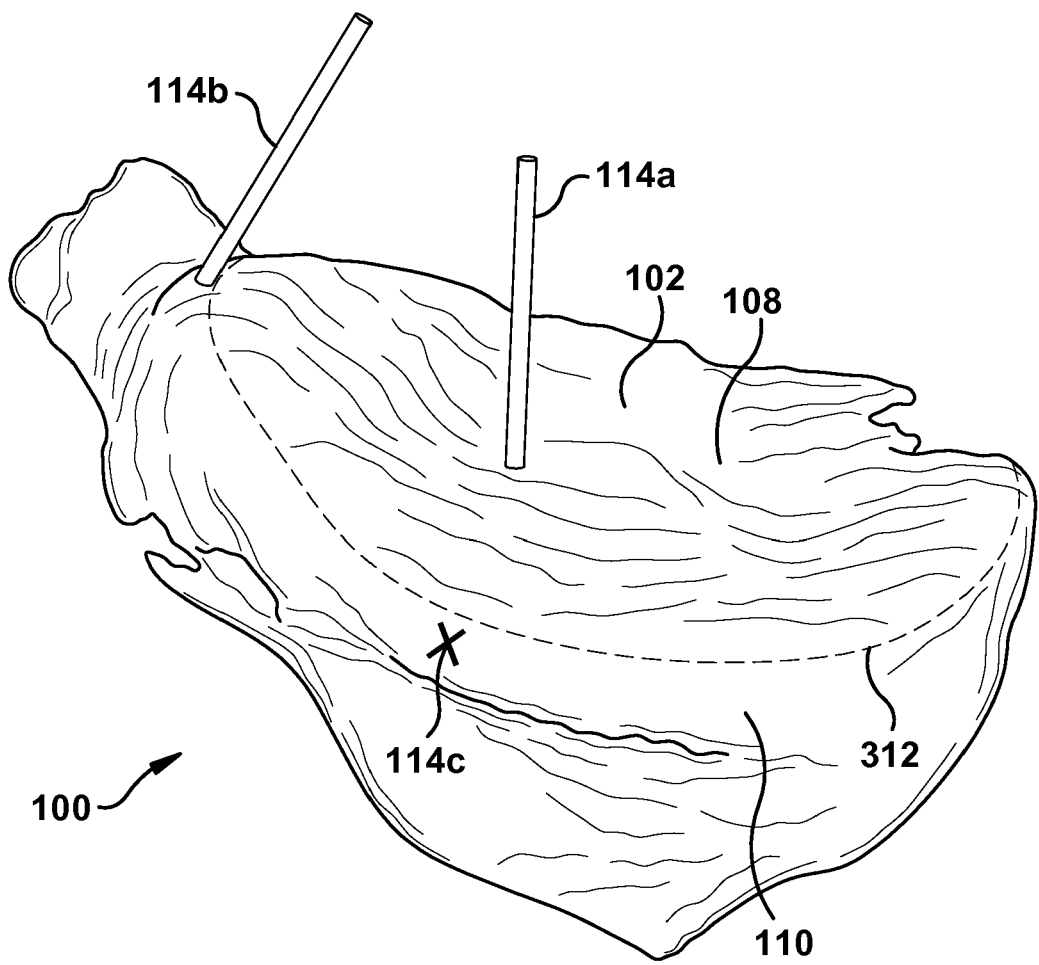
FIG. 3 is a partial perspective view of the example use environment of FIG. 1.

FIG. 3 is a partial perspective view of the scapula 100, with particular emphasis on the glenoid fossa 102. For the sake of discussion, the glenoid fossa 102 itself is referred to herein as a primary patient tissue area 108. That is, the primary patient tissue area 108 is a portion which directly receives an implant and/or is otherwise directly affected by a surgical procedure. In contrast, a secondary patient tissue area 110 is one which does not receive an implant and/or is not directly affected by a surgical procedure. In FIG. 3, the secondary patient tissue area 110 borders the primary patient tissue area 108 and is anatomically differentiated from the primary patient tissue area (i.e., the glenoid fossa 102) by the glenoid rim, indicated approximately by differentiation line 312. Here, the differentiation line 312 generally indicates an arbitrary (i.e., "depending on individual discretion") position along the continuous transition between the glenoid fossa 102 and the supporting structures (e.g., the glenoid rim, the glenoid neck, the base of the coracoid, and/or the glenoid wall). However, regardless of the precise position of the differentiation line 312 for a particular application of the present invention, one of ordinary skill in the art should be able to distinguish between a primary patient tissue area 108 (one which is directly affected by a surgical procedure) and a secondary patient tissue area 110 (one which is incidentally affected by a surgical procedure, if at all) for the purposes of the present invention.

A distinction is made herein between the primary and secondary patient tissue areas 108 and 110 because the present invention relates to the association of at least one landmark with at least one of the primary and secondary patient tissue areas. The term "landmark" is used herein to indicate any guiding aid which serves as a detectable indicator of a particular position on a "marked" substrate (here, the patient tissue). The landmarks discussed with respect to the present invention are presumed to be affixed or otherwise rigidly associated with a particular patient tissue so that a user can confidently maintain a sense of physical and/or visual orientation within the operative field. Suitable landmarks may include, but are not limited to, visual "written" marks (e.g., a thin layer of a substance left behind after contact with a crayon, surgical pen, or the like), other written marks outside the visual spectrum (e.g., a UV-fluorescent paint), guide pins, fasteners (e.g., screws, nails, staples, or the like), radioactive tags, bovie cautery burn marks, metallic or nonmetallic devices attached to the desired landmark site (e.g., a rivet, tack, or the like), or even modifications of the patient tissue itself (e.g., notches, inscribed lines, drill holes, or the like). Depiction of one type of landmark 114 in the Figures herein merely serves as an example and does not preclude the use of a different type of landmark, even in a similar use environment to those depicted, for a particular application of the present invention.

Three landmarks 114a, 114b, and 114c are shown in FIG. 3 as having been associated with the primary and secondary patient tissue areas 108 and 110. Landmarks 114a and 114b are three-dimensional pins which have been inserted into the primary and secondary patient tissue areas 108 and 110, respectively. Landmark 114c is a visible two-dimensional cross mark on the secondary patient tissue area 110.

Any landmark 114, regardless of type, will be located at a predetermined marking location with respect to the primary and/or secondary patient tissue areas 108 and 110. A three-dimensional landmark, like the marking pins shown as landmarks 114a and 114b in FIG. 3, may also have a predetermined marking trajectory which, like the marking location, holds some significance for the user. For example, landmarks 114a and 114b do not have parallel trajectories as depicted in FIG. 3. While the marking trajectory of a three-dimensional landmark 114 (i.e., one protruding noticeably from the patient tissue surface) might have no significance, the following discussion presumes, for ease of reference, that the marking trajectory of the three-dimensional landmark is intentionally provided and is held substantively constant during the tenure of the landmark at the marking location.

It is contemplated that a landmark 114 will normally be rigidly affixed to a particular marking location on the primary or secondary patient tissue area 108 or 110 in order to serve as a reliable lodestar for the user. However, in certain situations, the marking location of the landmark 114 may move (as seen from an outside point of reference) after placement, of its own accord, by action of a user, or by action of the substrate patient tissue, and these situations do not pass out of the domain of the present invention merely by virtue of such intentional or unintentional post-placement landmark motion.

The marking location and marking trajectory of each landmark 114 are predetermined by a user before the landmark is associated with the patient tissue. This predetermination may occur intraoperatively, as the user is able to directly see the condition of the surgical site. However, it is contemplated that a predetermination of the desired marking location and desired marking trajectory for each landmark 114 could be accomplished preoperatively, with reference to preoperative imaging of the patient tissue. For example, a system similar to that of co-pending U.S. patent application Ser. No. 13/282,550, filed Oct. 27, 2011, titled "System of Preoperative Planning and Provision of Patient-Specific Surgical Aids" and claiming priority to U.S. Provisional Patent Application No. 61/408,392, filed Oct. 29, 2010 and titled "System of Preoperative Planning and Provision of Patient-Specific Surgical Aids", the entire contents of both of which are incorporated herein by reference, or any suitable preoperative planning system could be used. In this manner, a user can create a patient tissue model for observation, manipulation, rehearsal, or any other pre-operative tasks.

The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface.

Once the user is satisfied with her preoperative planning tasks, virtual landmarks may be virtually placed on the patient tissue model. In order to transfer those virtual landmarks to the physical world for intra-operative use, a patient-specific apparatus (shown in FIG. 4 as a guide 416) may be at least partially customized responsive to preoperative imaging of the patient tissue. Accordingly, at least a part of the guide 416 is a patient-specific, single-use, bespoke component suited only for use at the indicated surgical site, though one of ordinary skill in the art could create a guide (not shown) which uses a patient-specific "disposable" structure connected to a stock, generic "reusable" carrier.

The patient's name, identification number, surgeon's name, and/or any other desired identifier may be molded into, printed on, attached to, or otherwise associated with the guide 416 in a legible manner. The guide 416 may be made by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling, computer numeric control ("CNC"), other rapid prototyping methods, or any other desired manufacturing process.

The guide 416 assists the user by associating a plurality of landmarks 114 with patient tissue, each landmark being associated with the patient tissue in at least one of a predetermined marking location and a predetermined marking trajectory. As depicted in FIGS. 4-7, a base 418 may have a lower base surface 520 contoured to mate with both the primary and secondary patient tissue areas 108 and 110 in a preselected relative orientation. The term "mate" is used herein to indicate a relationship in which the contours of two structures are at least partially matched or coordinated in at least two dimensions. In the described mating relationship depicted in FIGS. 4-7 as an example of the present invention, the lower base surface 520 mates or nests into contact with the surfaces of both the primary and secondary patient tissue areas 108 and 110 to provide the guide 416 with at least one of location and stabilization assistance with respect to the patient tissue.

The lower base surface 520 is spaced apart from an upper base surface 422 by a base body 424. A plurality of base apertures 526 extend between the upper and lower base surfaces 422 and 520 through the base body 424. The base apertures 526 are shown here as extending substantially longitudinally through the base body 424, but may have any desired orientation with respect to the base 418.

A plurality of guiding bosses 428 may protrude from the base 418 in certain configurations of the present invention. As shown in the Figures, the guiding bosses 428 protrude substantially longitudinally outward from the upper base surface 422, but the guiding bosses may have any desired orientation with respect to the base 418. Each guiding boss 428 has a guiding bore 428 extending therethrough. Each guiding bore 428 extends collinearly with a corresponding base aperture 526 to permit insertion of a landmark 114 through the guide 416. The term "insertion of a landmark through" is intended to encompass both a physical feeding of a three-dimensional landmark itself through the indicated structure for affixation to the underlying patient tissue (e.g., by penetration), as well as the temporary introduction of a marking device (e.g., a pen, bovie, rasp, other marking actuator or substance dispenser, or the like) through the indicated structure for affixation of a two-dimensional landmark 114 directly onto the patient tissue.

Each guiding bore 430 and corresponding base aperture 526 cooperatively defines at least one of the predetermined marking location and the predetermined marking trajectory (shown in FIG. 5 by trajectory lines 532) for an associated landmark 114. In the embodiment shown in FIGS. 4-7, at least one landmark 114 is guided by the guide 416 into engagement with a marking location in the primary patient tissue area 108 (via the rightmost guiding bore 430 in the orientation of FIG. 5) and at least one landmark is guided by the guide into engagement with a marking location in the secondary patient tissue area 110 (via the leftmost guiding bore 430 in the orientation of FIG. 5).

Figure 4:
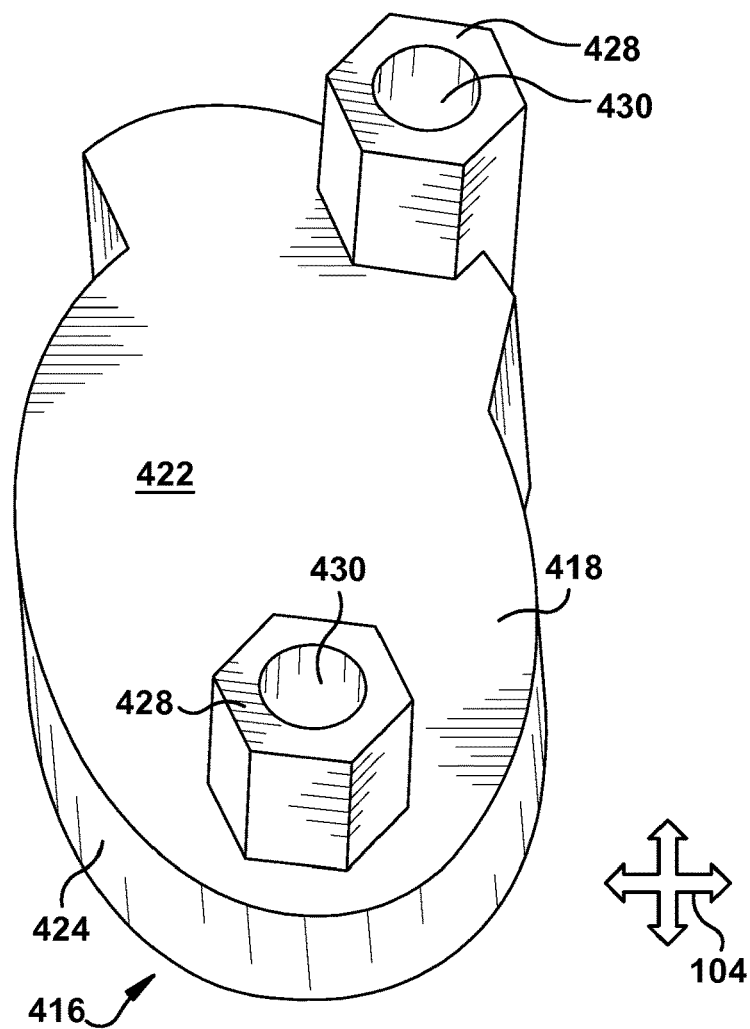
FIG. 4 is a top view of an embodiment of the present invention.
Figure 5:
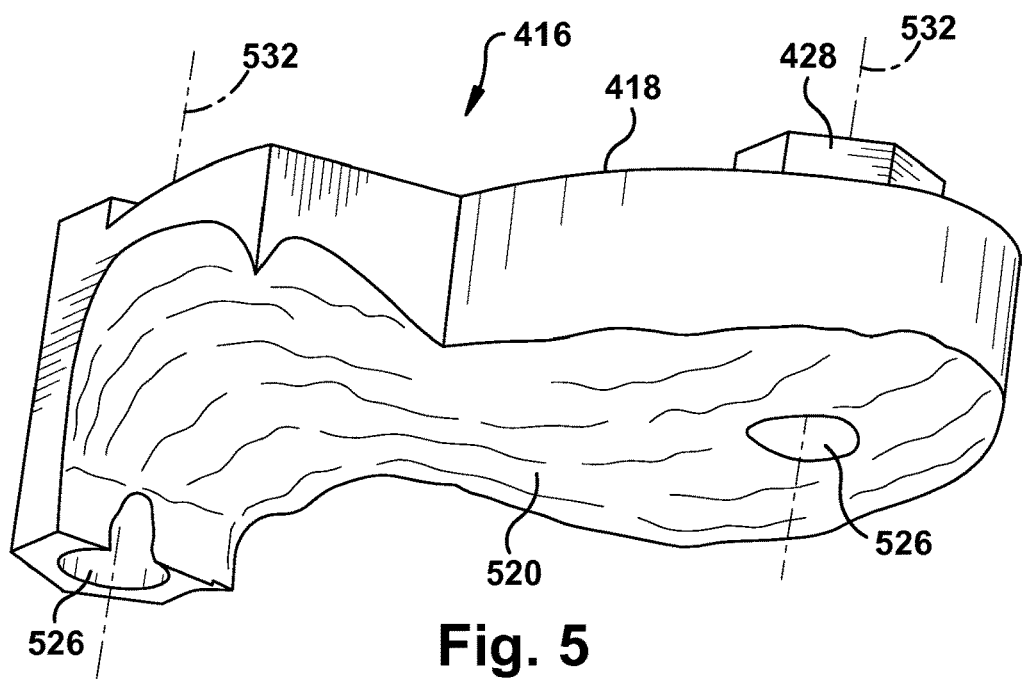
FIG. 5 is a perspective bottom view of the embodiment of FIG. 4 from a first side.
Figure 6:
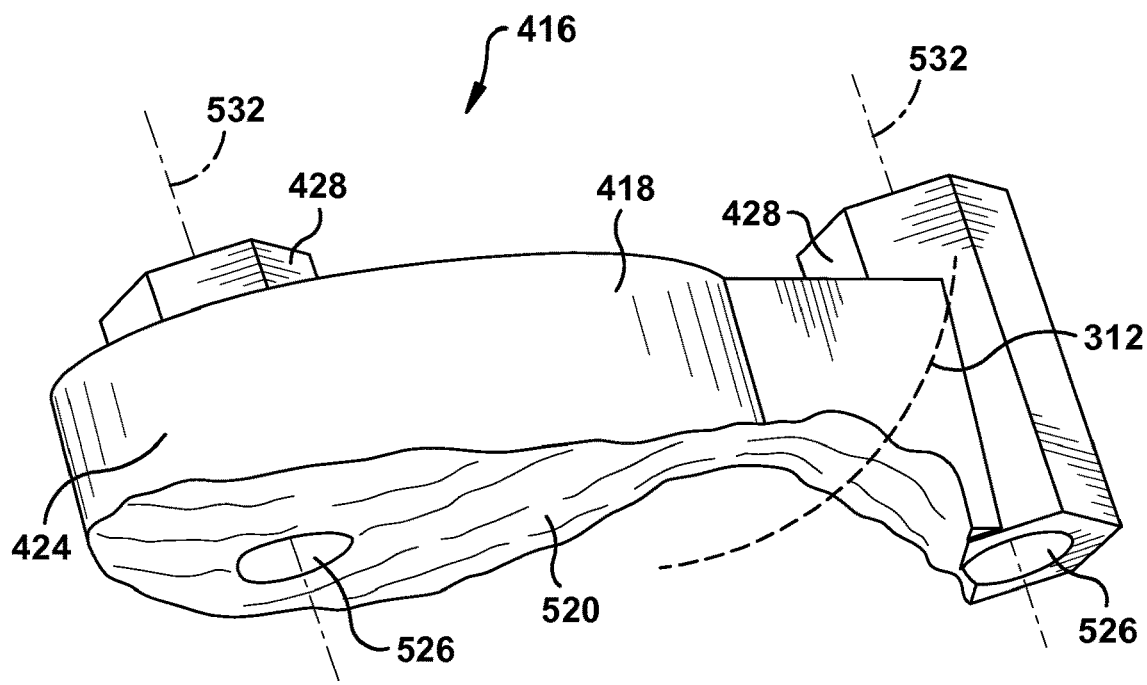
FIG. 6 is a perspective bottom view of the embodiment of FIG. 4 from a second side.

FIG. 6 depicts the guide 416 of FIG. 4 in a slightly different orientation in space, such that the contour of the lower base surface 520 may be seen in more detail. In the orientation of FIG. 6, the leftmost portion of the lower base surface 520 appears relatively broad and flat and is configured to mate with the surface of the glenoid fossa 102 (i.e., the primary patient tissue area 108 here). The differentiation line 312 from FIG. 3 is shown "ghosted" into FIG. 6 and extends somewhat into and out of the plane of the page due to the camber of the depiction in FIG. 6. With the addition of the differentiation line 312, it can be clearly seen that the rightmost portion of the lower base surface 520 does not mate with the primary patient tissue area 108, but instead dips sharply downward relative to the rest of the lower base surface to mate with the bordering secondary patient tissue area 110. Particularly when there is a "lip" or "rim" between the primary and secondary patient tissue areas 108 and 110, such as with the glenoid fossa 102, the ability of the lower base surface 520 to concurrently nest with both of these patient tissue areas may be helpful to the user in quickly and securely nestling the guide 416 down into the desired mating relationship with the patient tissue.

Figure 7:
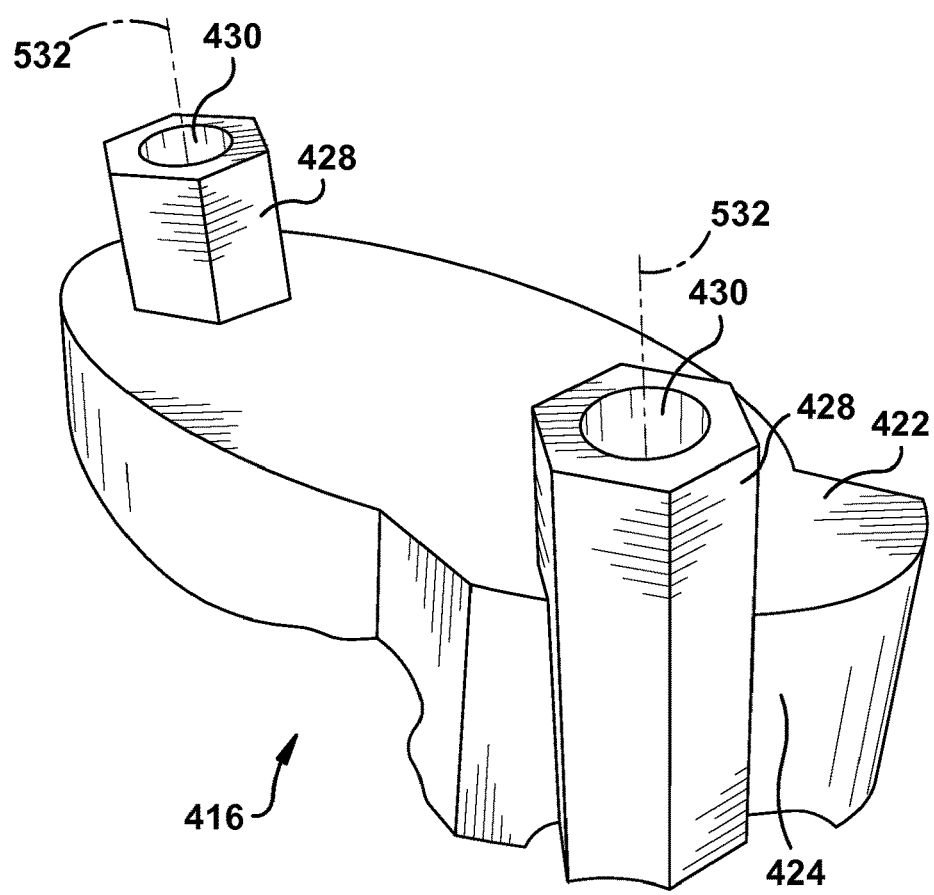
FIG. 7 is a perspective top view of the embodiment of FIG. 4 from the second side.

In FIG. 7, the upper base surface 422 and protruding guiding bosses 428 can be seen in detail. Particularly when a marking trajectory (such as that shown by trajectory lines 532) is defined by the base aperture 526, with or without the assistance of a guiding bore 430, it may be helpful for the guiding bosses 428 to provide a longer guiding structure for the inserted landmark 114. In other words, an elongate landmark 114 might precess within a relatively short base aperture 526, but the presence of the guiding boss 428 can support and stabilize insertion of the landmark to better guide the landmark along the predetermined marking trajectory.

Figure 8:
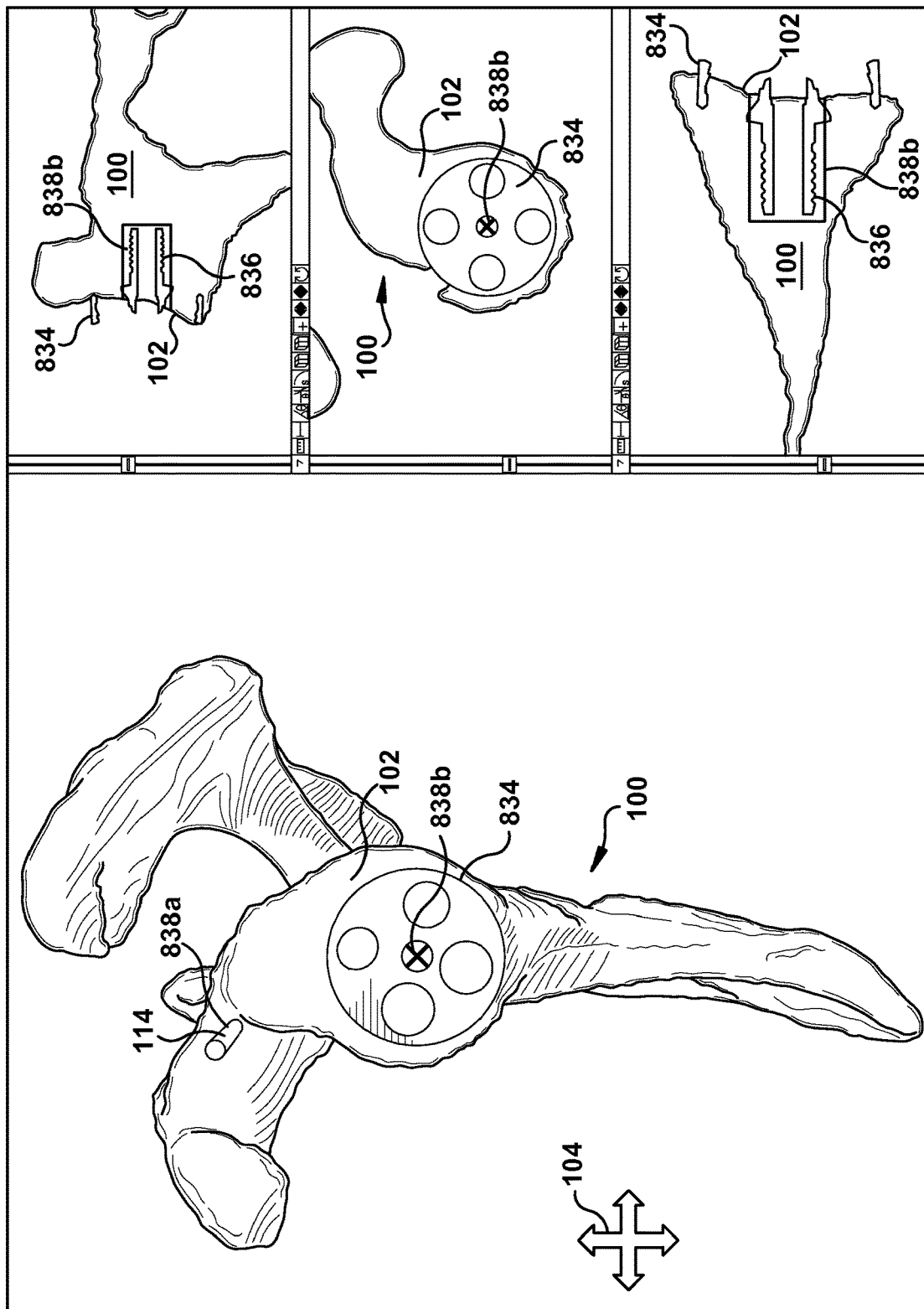
FIGS. 8-10 are example user views of a program for generating the embodiment of FIG. 4.
Figure 9:
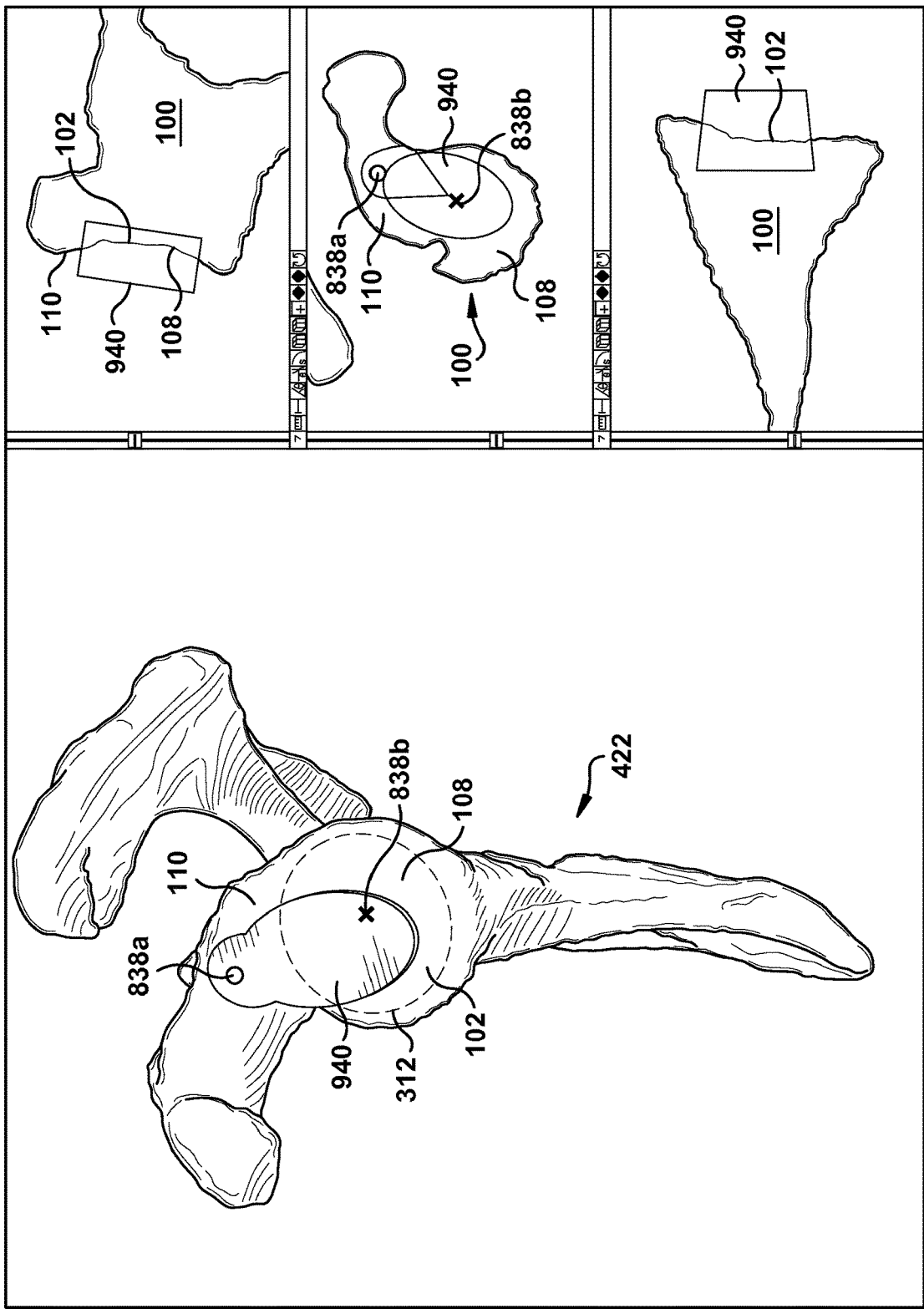
Figure 10:
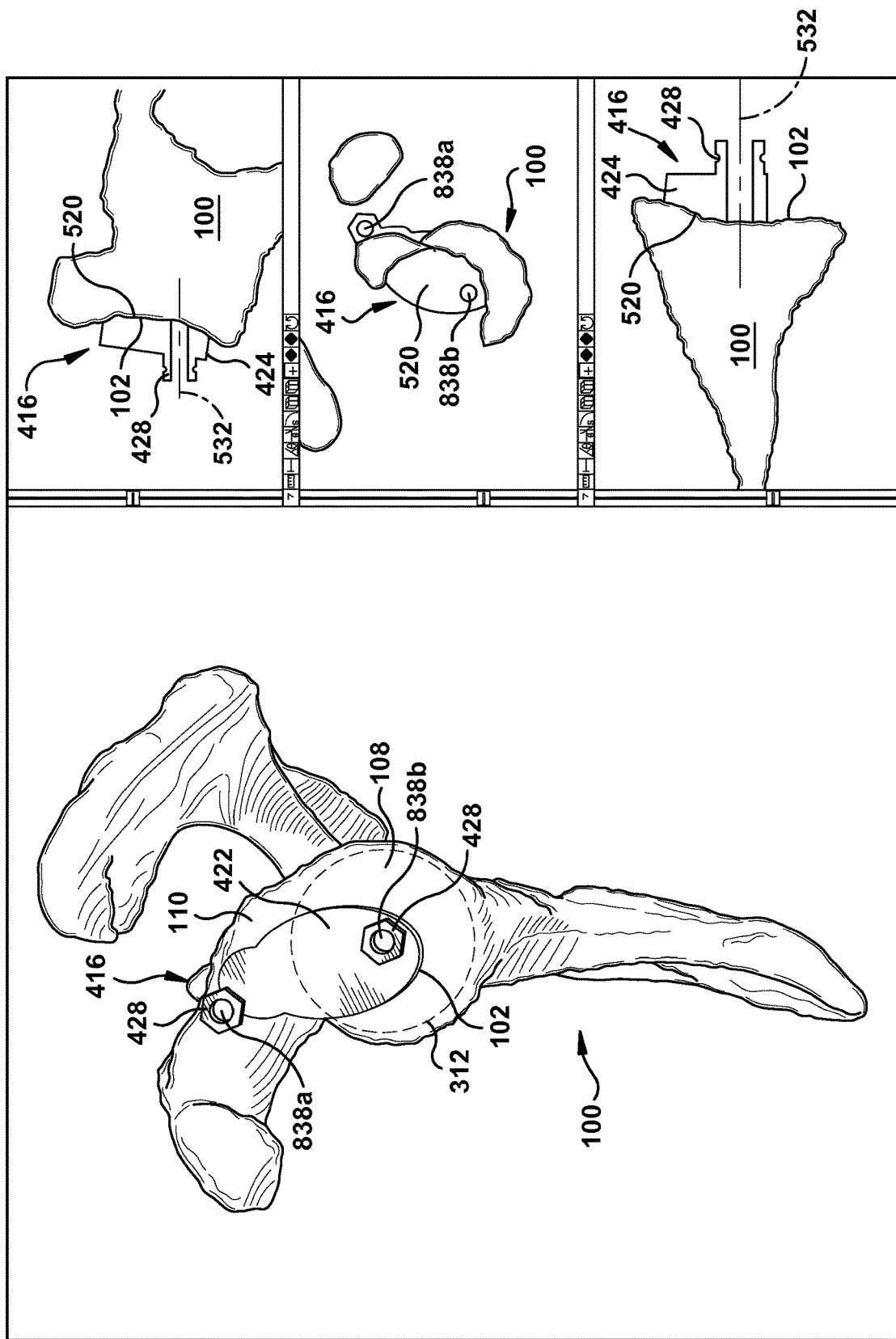

FIGS. 8-10 depict the generation of a suitable design for an example guide 416 during a preoperative planning procedure. FIGS. 8-10 are example user views of a computer program for implementing a method using the present invention, with a perspective view on the left side of each Figure and coronal, sagittal (looking distally from underneath the perspective view, as shown), and transverse views, respectively, from top to bottom on the right side of each Figure.

In FIG. 8, a stock glenoid implant 834 is shown associated with a glenoid fossa 102 of a patient's scapula 100, embodied in a model produced using preoperative imaging. The glenoid implant 834 may be virtually placed as desired on the scapula 100 by the user, or may be automatically placed by the computer program with or without a final check/adjustment by the user. The glenoid implant 834 appears to overlap with the glenoid fossa 102 in particularly the coronal (top right) and transverse (bottom right) views of FIG. 8, but this overlap (when present) is acceptable at the planning stage of FIG. 8 since the physical glenoid fossa 102 will be prepared via machining or other alteration(s) as desired during installation of the physical glenoid implant 834 at the surgical site, and this overlap will be corrected by removal of the interfering patient tissue. In fact, relatively precisely placed landmarks 114 are useful during many surgeries because the site preparation procedure commonly erodes, moves, or destroys natural landmarks which otherwise would help the user with placement or orientation during the surgical procedure.

Implant stem 836, visible in cross-section in the coronal and transverse portions of FIG. 8, is a tubular anchoring extension from the underside of the glenoid implant 834 which is inserted into the patient tissue of the glenoid fossa 102 during use. One consideration that a user may have during placement of the glenoid implant 834 using the computer program shown in FIGS. 8-10 is being able to locate the implant stem 836 in a solid portion of the patient's scapula 100. Another, similar consideration is the location of screws or other fasteners (not shown) which are commonly used to secure the glenoid implant 834 to the glenoid fossa 102. The user will want to ensure that the proper locations and trajectories are chosen for affixation of the selected fasteners into relatively robust areas of the patient's scapula 100. Once the glenoid implant 834 (including the implant stem 836 and the associated fasteners) has been virtually placed as desired into a final installation position, the user can decide where to place one or more landmarks 114, using the guide 416 and relatively early in the surgical process, to facilitate later tasks during the surgery. For example, the user of the FIG. 8 example may wish to place a guide pin as a landmark 114 at each of the marking locations 838 indicated by cross marks. As shown in FIG. 8, one marking location 838a is placed in the primary patient tissue area 108 and another marking location 838b is placed in the secondary patient tissue area 110. For certain surgical procedures, both of these locations may be marked as desired for bone preparation and final implant positioning. Landmarks 114 may be placed before the patient tissue is altered or modified, with the marking locations 838 corresponding to each landmark being specified during the preoperative surgical planning and/or simulation, or in any other suitable manner.

For example, a guide pin is displayed as a three-dimensional landmark 114 at the marking location 838a spaced apart from the glenoid implant 834 over the image of scapula 100 in FIG. 8, while an aperture or cavity formed in the scapula is shown as a two-dimensional landmark 838b (i.e., represented by a cross mark when seen from above or below) corresponding to a central portion of the glenoid implant in FIG. 8. In fact, the "negative" aperture-type landmark 838b of FIG. 8 is configured to receive a device shaft implant stem 836 of the glenoid implant 834, which helps to locate and stabilize the glenoid implant with respect to the scapula 100. One of ordinary skill in the art would readily be able to instead provide a "positive" pin- or shaft-type landmark (not shown) protruding from the scapula 100 and adapted to be received in a cavity (not shown) of another type of device, in an axle-type manner.

Optionally, the marking locations 838 may be chosen to comport to common landmark 114 placements to facilitate use of standard tools (not shown) with the guide 418. For example, two marking locations 838 may be provided to indicate a line bisecting the scapula 100 for that patient so that the user has a standardized reference line. In this example, then, generic surgical tools which use the scapula-bisecting line as a landmark in every patient will encounter a patient tissue which has been standardized, through use of personalized landmark 114 placements, to meet a universal expectation of the user. In other words, and more generally, the marking location 838 choices can be set for a particular patient tissue in order to compensate for any peculiarities of that patient tissue and accordingly provide the user with a surgical site that may be addressed using stock (i.e., not patient-specific) tools and/or techniques. This type of "universal registration" may be especially helpful in automation-assisted surgeries.

In FIG. 9, a user view of the computer program shows a guide blank 940 superimposed on the scapula 100. Since the guide 418 will be used to place the landmark(s) 114 before the surgical site is altered, the lower base surface 422 should be designed as a mirror image of the surface of the glenoid fossa 102, to mate with the primary and secondary patient tissue areas 108 and 110 as desired. The resolution of the preoperative imaging scans and the available precision of the chosen manufacturing method for the guide 416 will determine how precisely this mating is accomplished. As is apparent in FIG. 9, the guide blank 940 contacts and mates with both the primary and secondary tissue areas 108 and 110. The marking locations 838a and 838b identified in the view of FIG. 8 are represented as a small circle and a cross mark, respectively, on the guide blank 940 in FIG. 9.

Turning to FIG. 10, the areas of the guide blank 940 which overlap with the patient tissue of the scapula 100 have been removed by the computer program, generating the complex contour of the lower base surface 520 (most apparent in the coronal view). Additionally, base apertures 526 and corresponding guiding bosses 428 with guiding bores 430 have been placed at the desired marking locations 838, the base apertures and guiding bores being collinear to cooperatively define desired marking trajectory lines 532. Once the preoperative planning has been accomplished, through user input and/or automatic programming, the design of the guide 416 is complete and the guide can be manufactured and prepared for use (e.g., mechanically or chemically cleaned, cured, sterilized, or the like) using any suitable process(es).

FIGS. 11-15 depict various options for configurations of the guide 416. These different configurations, along with other (non-depicted) configurations, of guides 416 can be selected/designed and used by one of ordinary skill in the art to provide desired landmark-placement properties for different patient tissues. Structures of FIGS. 11-15 that are the same as or similar to those described with reference to FIGS. 4-10 have the same reference numbers. As with all alternate configurations shown and described herein, description of common elements and operation similar to those in previously described configurations will be omitted, for clarity. In the second configuration, shown in FIGS. 11-12, the guide 416 is relatively large compared to that of FIGS. 4-10

(although the Figures herein are not drawn to scale). As can be seen in the comparative views of FIGS. 10 and 12, the guide 416 of the second configuration (shown in situ in FIG. 12) covers more of the glenoid fossa 102 than does the guide 416 of the first configuration (shown in situ in FIG. 10). Additionally, the leftmost base aperture 526 and guiding bore 430 (as seen in the orientation of FIG. 12) is located substantially in an anterior portion of the secondary patient tissue area 110 for the second configuration, while the corresponding structures in the first configuration are located substantially more superiorly within the secondary patient tissue area 110.

Figure 12:
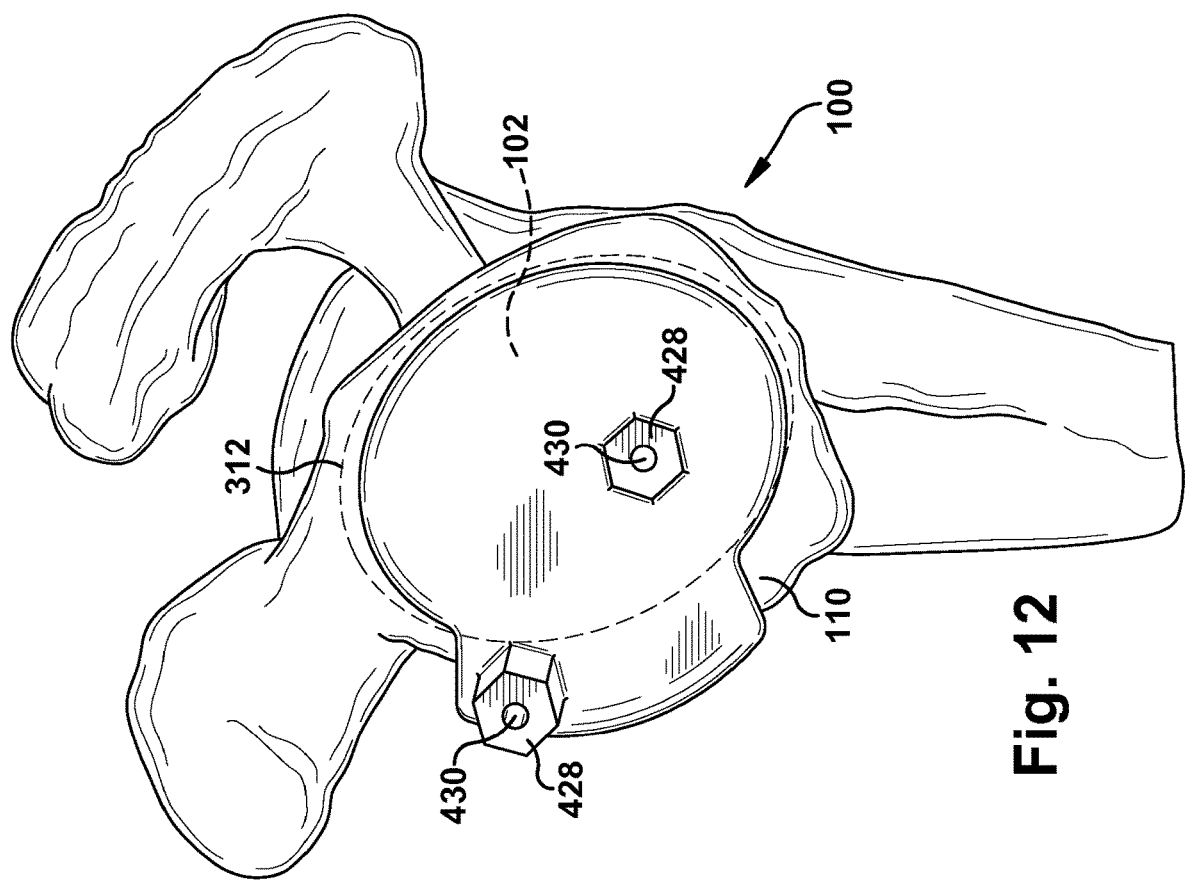
FIG. 12 is a front view of the embodiment of FIG. 11 in a second configuration in the example use environment of FIG. 2.
Figure 11:
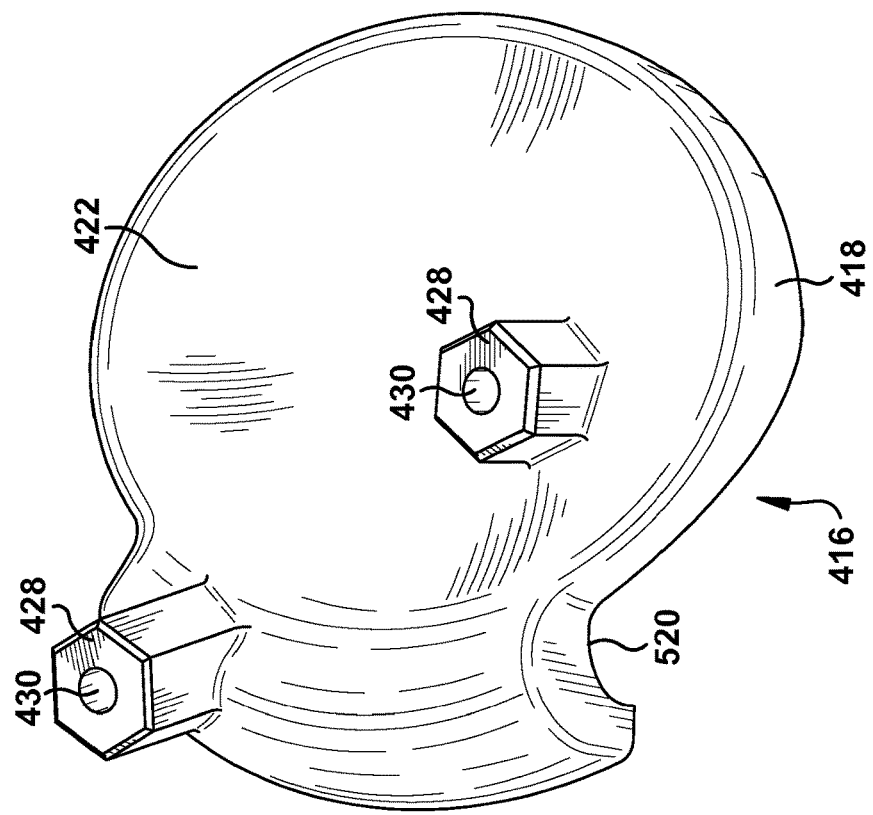
FIG. 11 is a front view of the embodiment of FIG. 4 in a second configuration.
Figure 13:
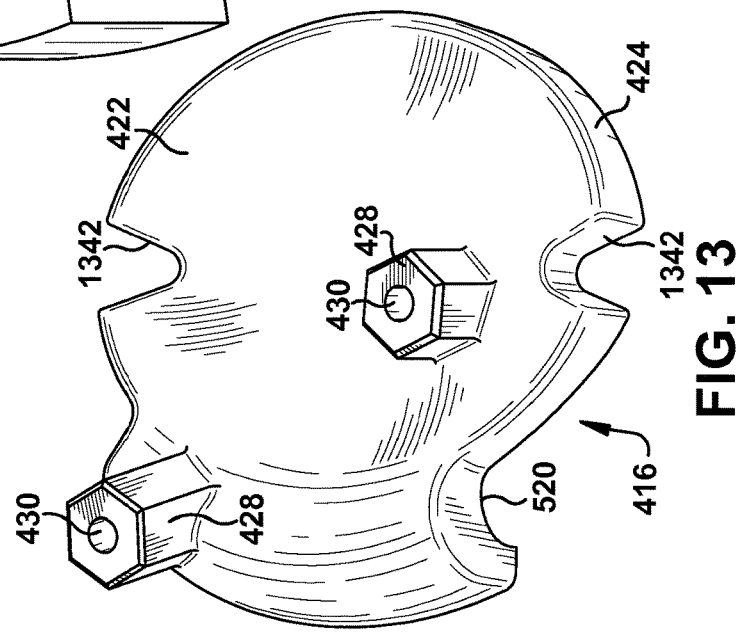
FIG. 13 is a top view of the embodiment of FIG. 4 in a third configuration.

The third configuration of the guide 416, shown in FIG. 13, seems similar to that of FIGS. 11-12, with the addition of at least one marking notch 1342. The marking notch(es) 1342 may be useful for guiding contact with the patient tissue for placing a two-dimensional (e.g., via a pen, bovie, crayon, or other marking device) or three-dimensional landmark 114 at a desired marking location 838, particularly if achieving a precise marking trajectory is not important.

Figure 14:
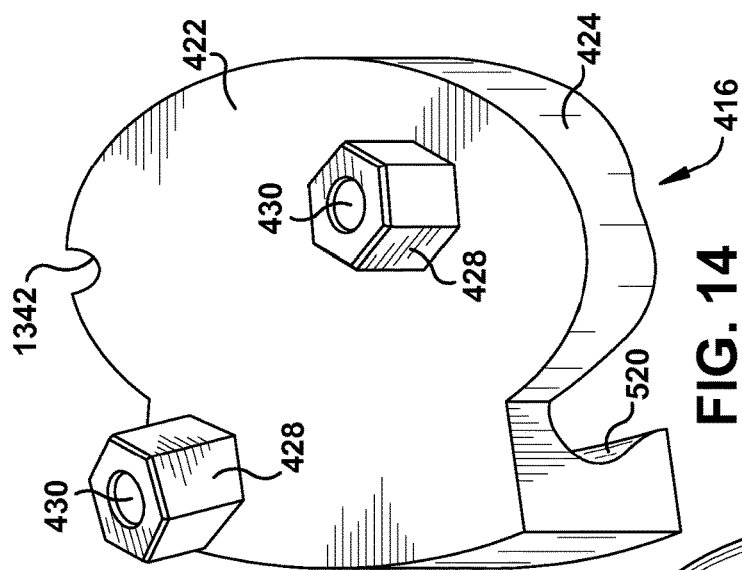
FIG. 14 is a top view of the embodiment of FIG. 4 in a fourth configuration.

FIG. 14 shows a fourth configuration of the guide 416 which includes features from several of the previously defined configurations. The guide 416 of FIG. 14 has a blockier shape than that of FIG. 13, which may provide efficiencies in design and/or fabrication. That is, the blockier shape of the fourth configuration guide 416 may be better suited to a design scheme involving the provision of a generic guide blank 940. In contrast, the contoured upper base surface 422 exhibited by the third configuration guide 416 requires more extensive smoothing and shaping operations (during the virtual modeling of the computer program and/or during physical manufacture), particularly if the base body 424 is configured to have a substantially uniform thickness by some degree of mirroring of the lower base surface 520 (dictated by the glenoid fossa 102) with the contour of the upper base surface 422. In the fourth configuration of FIG. 14, the marking notch 1342 of the guide 416 is somewhat rounded and may be operative to assist with placement of a three-dimensional landmark 114, such as a guide pin, at the marking location 838, optionally with some degree of imposed marking trajectory.

Figure 15:
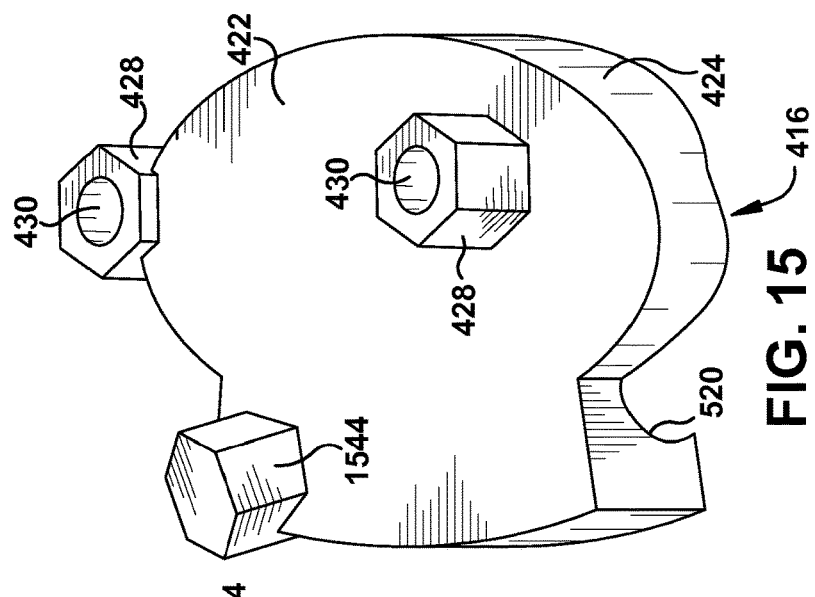
FIG. 15 is a top view of the embodiment of FIG. 4 in a fifth configuration.

A fifth configuration of the guide 416 is shown in FIG. 15. The guide 416 shown in FIG. 15 is similar to that shown in FIG. 16, with a guiding boss 428 in place of the marking notch 1342, and with the addition of a handling boss 1544. The handling boss 1544 protrudes from the base 418 and is configured for manipulation by the user to at least partially control a position of the guide 416. Sometimes the available maneuvering space in a surgical field is relatively restricted, and it may be useful for a forceps, socket driver (perhaps with a frictional fit or other feature to accept the handling boss 1544), Kocher tool, hemostat, or other user-manipulated handling tool (not shown) to selectively interact with the handling boss to hold the guide 416 steady and/or to move the guide 416 to a desired position. One or more features, such as indents, apertures, cavities, lugs, undercuts, or any other suitable structures could be provided to the handling boss 1544 to facilitate gripping of the guide 416 by any handling tool, in general, and/or by a particular handling tool (perhaps one chosen in conjunction with the chosen glenoid implant 834). Optionally, the handling boss 1544 may also be a guiding boss 428. However, in some situations it will be desirable for each of the guiding bosses 428 to be accessible for landmark 114 placement at the same time that a handling tool is engaged with the handling boss 1544, so the handling boss could be a separate structure in those situations.

Regardless of the specific configuration chosen for a particular patient, the guide 416 will generally be used relatively early in the surgical procedure. The guide 416 has a base 418 at least partially customized (e.g., custom-manufactured and/or custom-configured) responsive to preoperative imagining of the patient tissue. The base 418 of the guide 416 is mated with at least one of the primary and secondary patient tissue areas 108 and 110 in a preselected relative orientation. When the base 418 is mated with both the primary and secondary patient tissue areas 108 and 110, the mating may be concurrent for both those patient tissue areas.

At least one landmark 114 is guided by the guide 416 to a marking location 838 in the primary patient tissue area 108 and fixed to the primary patient tissue area 108 in at least one of a predetermined marking location 838 and an predetermined marking trajectory, such as by passing of the landmark 114 along a marking notch 1342 or through a base aperture 526 (optionally with the assistance of a guiding bore 430). Optionally, at least one additional landmark 114 may be guided by the guide 416 to a marking location 838 in the secondary patient tissue area 110 and fixed to the secondary patient tissue area 110 in at least one of a predetermined marking location 838 and an predetermined marking trajectory, such as by passing of the additional landmark along a marking notch 1342 or through a base aperture 526 (optionally with the assistance of a guiding bore 430).

Once the desired number of landmarks 114 are affixed to the primary and/or secondary patient tissue areas 108 and 110, the guide 416 is removed from the surgical site in any suitable manner, optionally with the assistance of a handling boss 1544. When at least one landmark 114 is a guide pin or other elongate three-dimensional structure, the guide pin may deflect, if needed, to allow the guide 416 to be lifted longitudinally off the protruding end guide pin. Alternately, the guide 416 may include at least one frangible portion to allow substantially laterally-oriented removal of the guide 416 from around the guide pin. As another example, the guide 416 could include one or more slots (not shown) to allow removal of the guide by sliding the guide sideways away from the guide pin.

Regardless of the manner in which the guide 416 is removed from the primary and secondary patient tissue areas 108 and 110, the landmark(s) 114 remain behind and the surgical site attains a configuration akin to that shown in FIG. 3. The user can then proceed with the surgical procedure with confidence that the landmark(s) 114 are substantially located as configured in the preoperative plan. The patient tissue at the primary patient tissue area 108 can be altered and the landmark(s) 114 that remain as placed using the guide 416 can be used to orient such alteration or for any other surgical task. For example, a prosthetic implant (such as the glenoid implant 834, when the patient tissue is a scapula 100) may be placed, optionally with the assistance of another patient-specific guide, such as that disclosed in co-pending U.S. patent application Ser. No. 13/282,495, filed Oct. 27, 2011, titled "System and Method for Assisting with Attachment of a Stock Implant to a Patient Tissue" and claiming priority to U.S. Provisional Patent Application No. 61/408,324, filed Oct. 29, 2010 and titled "System and Method for Assisting with Attachment of a Stock Implant to a Patient Tissue", the entire contents of both of which are incorporated herein by reference.

FIGS. 16-24 depict a guide 416' according to certain aspects of a second embodiment of the present invention. The guide 416' of FIGS. 16-24 is similar to the guide 416 of FIGS. 1-15 and therefore, structures of FIGS. 16-24 that are the same as or similar to those described with reference to FIGS. 1-15 have the same reference numbers with the addition of a "prime" mark. Description of common elements and operation similar to those in the previously described first embodiment will not be repeated with respect to the second embodiment.

Figure 16:
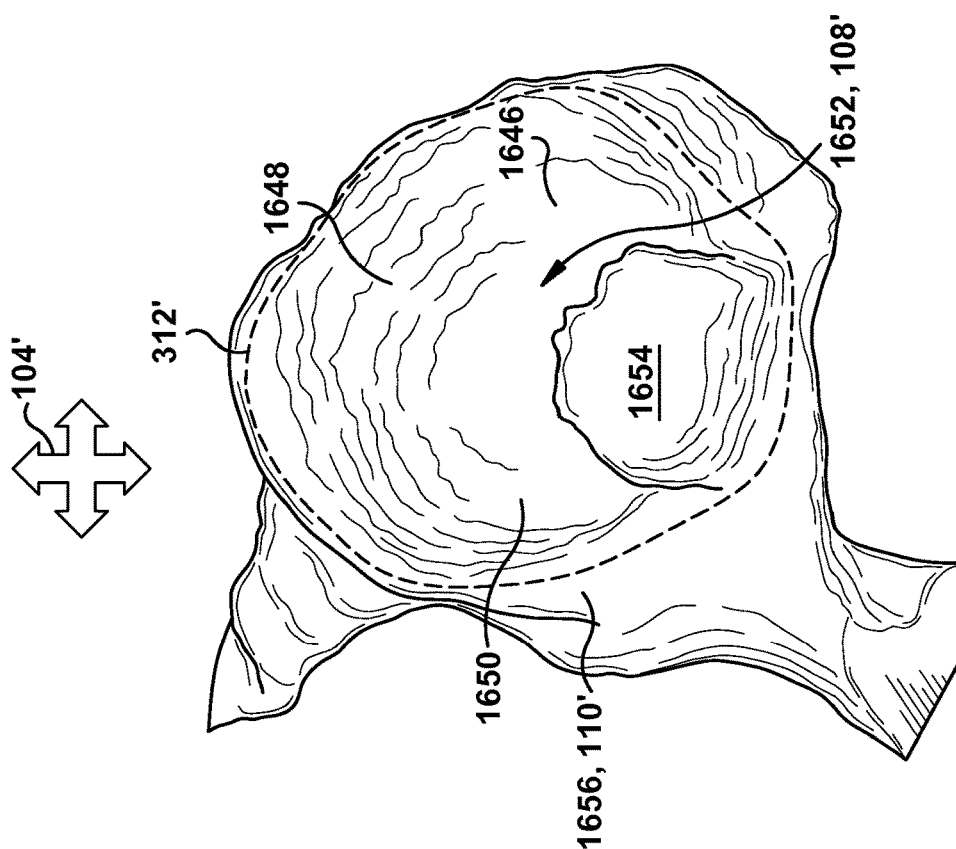
FIG. 16 is a top view of a second example use environment.

FIG. 16 depicts an example use environment for the guide 416' of the second embodiment. Directional arrow 104' indicates the superior/inferior and anterior/posterior directions. The body of ischium, body of ilium, and body of pubis are shown generally at 1646, 1648, and 1650, respectively. The acetabulum 1652 (here, the primary patient tissue area 108'), which is formed in part by these three bodies 1646, 1648, and 1650, has a recessed acetabular fossa 1654 and is surrounded by an acetabular margin 1656 (here, the secondary patient tissue area 110', shown approximately in FIG. 16 as being outside the dashed differentiation line 312').

Figure 17:
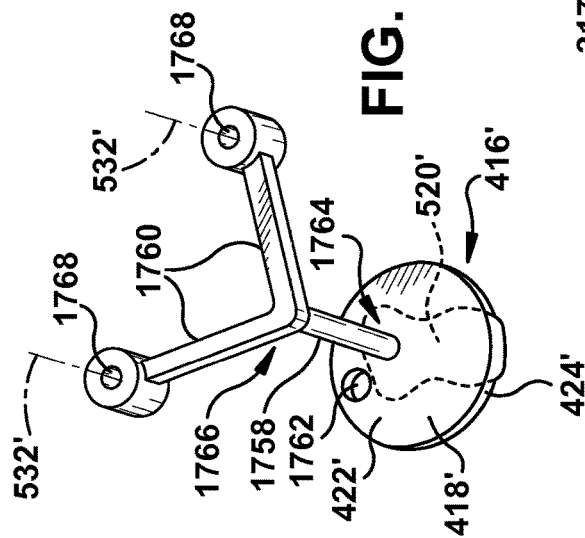
FIG. 17 is a top view of an embodiment of the present invention.
Figure 18:
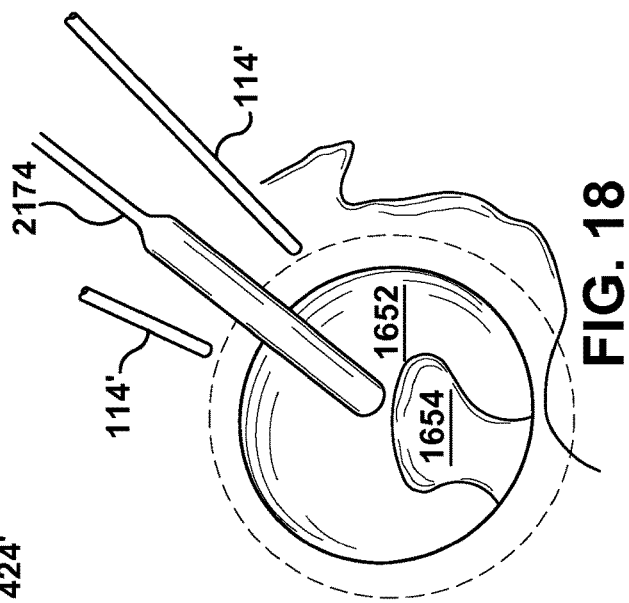
FIG. 18 is a top view of the use environment of FIG. 16 as modified through the use of the embodiment of FIG. 17.

In accordance with the present invention, FIG. 17 depicts a guide 416' including a base 418', a stem 1758, and at least one spacing arm 1760. The base 418' has a lower base surface 520' (shown partially in phantom line in FIG. 17) spaced apart from an upper base surface 422' by a base body 424'. The lower base surface 520' is contoured to mate with the acetabulum 1652 in a preselected relative orientation thereto. The base 418' may include a base guide aperture 1762 configured to guide placement of a landmark 114' inserted at least partially therethrough in at least one of a predetermined marking location and a predetermined marking trajectory, the marking location being in the primary patient tissue area 108'.

The stem 1758 has longitudinally separated first and second stem ends 1764 and 1766, respectively. The first stem end 1764 is attached directly to the base 418', either permanently or removably. The stem 1758 extends longitudinally upward from the base 418' (substantially out of the plane of the paper, in FIG. 17).

At least one spacing arm 1760 (two shown) is attached directly to the second stem end 1766, either permanently or removably. Each spacing arm 1760 is longitudinally spaced from the base 418' and has an arm guide aperture 1768 laterally spaced from the stem 1758. The arm guide aperture 1768 is configured to guide placement of a landmark (not shown in this Figure) inserted at least partially therethrough at a predetermined landmark trajectory (represented by trajectory line 532'). The spacing arm(s) 1760 are shown in the Figures as extending orthogonally from the stem 1758 at the second stem end 1766, in order to place landmarks 114' in the acetabular margin 1656 (the secondary patient tissue area 110') as will be discussed below. The spacing arm(s) 1760 could extend at any suitable angle or position from the stem 1758, or could even be smoothly formed as a single integral piece with the stem. In the latter event, the second stem end 1766 may not be clearly delineated from the spacing arm(s) 1760.

The stem 1758 and spacing arm(s) 1760 could have any of a myriad of configurations, depending upon the application of the present invention. A spacing arm 1760 is used herein to indicate any structure which is located at some distance from base 418' contacting a primary patient tissue area 108', and the spacing arm includes structure which can guide a landmark 114' to a secondary patient tissue area 110'. A stem 1758 is used herein to indicate any structure which extends between and connects the base 418' and at least one spacing arm 1760.

The guide 416' may be at least partially customized responsive to preoperative imaging of the patient tissue. For example, the lower base surface 520' of the base 418' could be at least partially configured through the use of computer tomography ("CT") data of the patient tissue to have a longitudinally downward-protruding portion corresponding to the acetabular fossa 1656. Additionally or alternatively, the lower base surface 520' could be at least partially configured through use of patient scans including digital or analog radiography, magnetic resonance imaging, or any other suitable imaging means. The patient tissue preoperative images are optionally displayed for review and manipulation before/during configuration of the lower base surface 520', such as through the use of a computer or other graphical workstation interface described above with reference to the first embodiment of the present invention. The configuration of the lower base surface 520' is described herein as being performed using three-dimensional images; however, one or more two-dimensional depictions of the patient tissue may also or instead be consulted during configuration of the lower base surface 520' or any other preoperatively configured structure herein.

The lower base surface 520' is configured to mate with a primary patient tissue surface 108', as will be discussed below. In the described mating relationship, the lower base surface 520' mates or nests into contact with the surface of the acetabulum 1652 to provide the base 418' with at least one of location and stabilization assistance with respect to the patient tissue. Though the lower base surface 520' is shown herein as covering a substantial portion of the acetabulum 1652, the lower base surface 520' may contact any suitable portion of the primary patient tissue area 108' sufficient to stabilize the guide 416' in a desired manner.

FIGS. 19-21 depict a guide 416' which is a second configuration of the embodiment of the present invention in the second embodiment of FIG. 17. The guide 416' of FIGS. 19-21 mainly differs from the guide 416' of FIG. 17 in the provision of at least one outrigger 1770 as an extension of the base 418'. The underside (tissue-contacting) surface of each outrigger 1770 forms a portion of the lower base surface 520' and is accordingly contoured to mate with a portion of the acetabulum 1652' (the primary patient tissue surface 108') and the surrounding secondary patient tissue surface 110'. For example, and as shown in the bottom view of FIG. 20, the outrigger(s) 1770 may extend laterally beyond the remaining acetabular-contacting portion of the base 418'. The outrigger(s) 1770 shown in FIGS. 19-21 may contact, or even hook over, the acetabular margin 1656' to assist with positioning and/or stabilizing of the guide 416' as shown in the cross-sectional side view of FIG. 21. The side view of FIG. 19 and the bottom view of FIG. 20 also clearly show a protrusion 1972 formed by the contour of the lower base surface 520' and shaped to mate with the acetabular fossa 1654 (shown in FIG. 16). Because each patient's bone structure is unique, at least a portion of the guide 416' (e.g., the outriggers 1770 and lower base surface 520') is customized responsive to preoperative imaging of the patient tissue.

FIG. 21 also shows an orthopedic guidewire 2174 acting as a landmark. One example of a suitable guidewire 2174 is disclosed in co-pending U.S. patent application Ser. No. 13/178,324, filed Jul. 7, 2011, titled "Method and Apparatus for Providing a Relative Location Indication During a Surgical Procedure" and claiming priority to U.S. Provisional Patent Application Ser. No. 61/362,722, filed Jul. 9, 2010, and titled "Method and Apparatus for Providing a Relative Location Indication During a Surgical Procedure", the contents of both of which are hereby incorporated by reference in their entirety. Additionally, FIG. 21 shows a pair of conventionally-configured guide pins acting as three-dimensional landmarks 114', though any suitable number, combination, and/or types of two- or three-dimensional landmarks 114' and/or guidewires may be provided for a particular use environment of the present invention, and may be associated with either or both of the base guide aperture(s) 1762' and the arm guide aperture(s) 1768'.

At least a portion of the guidewire 2174 is insertable through the base guide aperture 1762' and into the underlying acetabulum 1652' when the guide 416' is mated with the patient tissue in the preselected relative orientation. Similarly, at least a portion of each of the landmarks 114' is insertable through the arm guide aperture 1768' and into the underlying second patient tissue area 110', shown here as being located just beyond an acetabular margin 1656', when the guide 416' is mated with the patient tissue in the preselected relative orientation.

A distal end 2176 of the landmark 114' or guidewire 2174 is configured to remain inserted into the patient tissue when the guide 416' is removed from the patient tissue. It is contemplated that the base guide aperture 1762' and/or arm guide aperture 1768' will be sized to pass over the respective landmark 114' or guidewire 2174, leaving these guiding landmark structures in place such as in the configuration shown in FIG. 18. The landmark(s) 114' and/or guidewire(s) 2174 may remain in place for as long as the user desires, though normally will be removed from the patient's body before the surgical procedure is concluded. The landmark(s) 114' and/or guidewire(s) 2174 also may be used for any reason in conjunction with any type or number of processes, during or after the surgical procedure in which they were installed. A common guiding function for a landmark 114' or guidewire 2174 is to guide the positioning of another structure, either directly (via contact) or indirectly (spaced apart from the guided structure).

FIGS. 22-24 depict a guide 416' which is a third configuration of the second embodiment of the present invention and combines features of both the previous configurations of the second embodiment, as well as some features of the guide 416 of the first embodiment. The guide 416' of FIGS. 22-24 has a very complex base structure with a bifurcated lower base surface 520' which concurrently contacts at least a portion of a primary patient tissue area 108' (i.e., contacts an acetabulum 1652 with the leftmost portion of the lower base surface, as shown in the orientation of FIG. 23) and at least a portion of a secondary patient tissue area 110' (i.e., contacts an acetabular margin 1656 with the rightmost portion of the lower base surface, as shown in the orientation of FIG. 23). A plurality of guiding bosses 428' are provided to the guide 416' of FIGS. 22-24, including two guiding bosses located on an extended portion 2278 of the base body 424' to place landmarks 114' in the secondary patient tissue area 110' and one guiding boss located on a central portion 2280 of the base body to place a landmark 114' in the primary patient tissue area 108'.

The guiding boss 428' located on the central portion 2280 of the base body 424' is noticeably longer than the other guiding bosses, and may serve several functions for the guide 416'. The guiding boss 428' located on the central portion 2280 of the base body 424' may guide a landmark 1114 through a guiding bore 430' thereof; may guide a rasp, drill, or other tissue modification tool (not shown) therethrough, optionally providing a "stop" function to limit insertion of the tissue modification tool into the underlying patient tissue; and/or may serve as a handling boss for user manipulation by hand and/or with a handling tool.

FIGS. 25-29 depict a guide 416" according to a third embodiment of the present invention. The guide 416" of FIGS. 25-29 is similar to the guide 416 of FIGS. 1-15 and therefore, structures of FIGS. 25-29 that are the same as or similar to those described with reference to FIGS. 1-15 have the same reference numbers with the addition of a double "prime" mark. Description of common elements and operation similar to those in the previously described first and second embodiments will not be repeated with respect to the second embodiment.

The guide 416" of the third embodiment of the present invention may be used both for associating a plurality of landmarks 114" with a patient tissue in at least one of a predetermined marking location and a predetermined marking trajectory, and for guiding the removal of a predetermined amount of resection patient tissue and rearrangement of a remaining patient tissue, as will be described. One example of a potential use environment for the guide 416" of the third embodiment is in conjunction with a surgical procedure to correct a congenital or acquired orthopedic malunion.

FIGS. 25-26 depict a guide 416" in a first configuration in front and side views, respectively, in a use environment of a patient tissue forming at least a portion of a patient tissue such as, but not limited to, a femur, humerus, radius, ulna, tibia, fibula, metatarsal, phalange, another type of long bone shaft, a flat bone such as the mandible, a facial bone, a scapula body, a bone of the wrist or ankle, or any other patient tissue. In these Figures, the primary patient tissue area 108" is a resection patient tissue 108" (shaded in FIG. 26) and the secondary patient tissue area 110" is a remaining patient tissue 110". The guide 416" of FIGS. 25-26 is configured to contact the resection patient tissue 108" and the remaining patient tissue 110" and to guide surgical contact with the patient tissue.

The guide 416" of FIGS. 25-26 has a base 418" having a lower base surface 520" contoured to mate with both the resection and remaining patient tissues 108" and 110" in a preselected relative orientation. The lower base surface 520" is spaced apart from an upper base surface 422" by a base body 424", as shown in FIG. 26.

As shown in FIGS. 25-26, at least one base aperture 526" (two shown here) guides a landmark 114" into contact with the underlying tissue surface in at least one of a predetermined marking location 838" and a predetermined marking trajectory. A plurality of first guide cutting guide apertures 2582 extend between the upper and lower base surfaces 422" and 520" through the base body 424" to permit penetration of at least one cutting tool (shown schematically at 2584) through the guide 416". The cutting guide apertures 2582 each define at least one cutting plane location and cutting plane orientation for the cutting tool 2584 to make at least one resection cut into the patient tissue.

More specifically, the guide 416" is configured to cut the resection patient tissue 108" for removal from the remaining patient tissue 110". The resection patient tissue 108" is shaded in the Figures, and the cutting plane locations and orientations are chosen to correspond to the borders of the resection patient tissue. Because the resection patient tissue 108" in the Figures is located intermediate two areas of remaining patient tissue 110", at least two cutting plane locations and orientations are needed to excise the resection patient tissue 108". If there were no remaining patient tissue 110" to one side (e.g., the topmost side in the orientation of FIG. 26), only one cutting plane location and orientation would be needed to sever the resection patient tissue 108". However, the latter situation would not be a true case of correction of a malunion, but merely an amputation. A patient-specific guide 416" could be produced and used for an amputation if desired. However, though not excluding an amputation situation from application of a guide 416", this description presumes for ease of discussion that at least two cuts will be made to excise an area of resection patient tissue 108" from a surrounding area of remaining patient tissue 110".

Optionally, and as shown in FIG. 26, at least one guiding boss 428" may protrude from the upper base surface 422" in association with at least one of the base apertures 526" and the cutting guide apertures 2582, as shown in FIG. 26. The guiding bosses 428" shown in FIG. 26 may be helpful in avoiding precession of the cutting tools 2584 and thereby assist in guiding the cutting tools to make accurate cuts according to the preoperative plan embodied in the guide 416".

Once the resection patient tissue 108" has been cut and removed from the remaining patient tissue 110", the remaining patient tissue can be rearranged to correct two dimensions of deformity. From the deformed position of FIG. 26, therefore, the remaining patient tissue 110" areas can be collapsed together after removal of the shaded resection patient tissue 108" for correction in both the proximal-distal and superior-inferior dimensions. Accordingly, the patient tissue shown in FIG. 27 is composed entirely of remaining patient tissue and is substantially cylindrical along a superior-inferior axis 2786.

If there still remains a third degree of deformity, such as rotation about the superior-inferior axis 2786, to be corrected, then an optional guide 416" having a second configuration may be provided as shown in FIGS. 27-28A, the guide 416" of the second configuration being configured to guide surgical contact with the remaining patient tissue 110" after removal of the resection patient tissue 108". The guide 416" has a lower base surface 520" contoured to mate with the remaining patient tissue 110" in a preselected relative orientation after removal of the resection patient tissue 108". A plurality of base apertures 526" permit insertion of at least one landmark (two shown here, at 114a" and 114b") through the guide 416", the inserted landmarks either being extant at the surgical site before the guide of the second configuration is introduced or being inserted with the assistance of the guide of the second configuration.

At least one of the base apertures 526" of the guide 416" of the second configuration defines at least one of the predetermined marking location and the predetermined marking trajectory for a landmark 114a", 114b". For example, and as shown in the front view of FIG. 27 and the corresponding top view of FIG. 28A, the two landmarks 114a" and 114b" have substantially different marking locations and marking trajectories for their penetration into the remaining patient tissue 110". The landmarks 114a" and 114b" can therefore be used as indicators to aid in correction of the third degree of deformity.

Namely, one portion of the remaining patient tissue 110' can be rotated about the superior-inferior axis 2786 (e.g., as indicated by rotation arrow 2888). Because the resection patient tissue 108" was fairly recently removed, an excision seam 2790 (visible in FIG. 27) separates the upper and lower (in the orientation of FIG. 27) portions 2792 and 2794, respectively of the remaining patient tissue 110" and permits relative rotation of those portions to correct the third degree of deformity.

Due to preoperative planning of the desired third-dimension rotation and embodiment of that planning in the guide 416" of FIGS. 27-28A, the landmarks 114a" and 114b" can be placed in the respective upper and lower portions 2792 and 2784 of the remaining patient tissue 110" at trajectories that help guide the rotation during the surgery. For example, and as shown in the sequence of FIGS. 28A-28B, the landmarks 114a" and 114b" can be placed relatively askew in the remaining patient tissue 110" at predetermined marking trajectories (as shown in FIG. 28A). Relative rotation of the upper and lower portions 2792 and 2784 about the superior-inferior axis 2786 then will reposition the landmarks 114a" and 114b" into a second orientation with respect to one another—such as the substantially parallel orientation shown in FIG. 28B—to indicate to the user that the desired third-dimension rotation has been achieved. This second orientation can be approximated by the user's own observation or can be measured or otherwise subjectively indicated.

It is contemplated that the landmarks 114a" and 114b" will each be substantially rigidly held within its respective upper and lower portions 2792 and 2784 of the remaining patient tissue 110", so as not to introduce an unwanted amount of inaccuracy into the rotation procedure. However, one of the upper and lower portions 2792 and 2794 might be configured to move with respect to the guide 416", with the respective landmark 114a" or 114b" precessing therein, during the rotation procedure.

Optionally, at least one base aperture 526 of the guide 416" of the second configuration may also or instead define a location and/or trajectory for insertion of a fastener (not shown) into the remaining patient tissue 110". Accordingly, the guide 416" may be configured to guide the placement of at least one fastener to retain the remaining patient tissue in a desired final arrangement.

The guide 416" of the second configuration might also or instead include at least one cutting guide aperture 2582 to permit penetration of a cutting tool 2584 through the guide 416". In this instance, the guide 416" would be configured to define at least one cutting plane location and orientation for a cutting tool 2584 to make at least one secondary cut into the remaining patient tissue 110", the secondary cut being configured to assist with the correction of the third dimension of deformity.

FIG. 29 depicts a third configuration of a guide 416" according to the third embodiment of the present invention. In FIG. 29, the guide 416" is configured to assist with correction of a malunion or other deformity in the head of a femur, humerus, tibia, phalange, mandible, scapula, or any other suitable bone or other patient tissue. The guide 416" of the third configuration 416" can be used similarly to the guides 416" of the first and second configurations.

FIGS. 30-39 depict a guide 416' according to certain additional aspects of the second embodiment of the present invention. The guide 416' of FIGS. 30-37 is similar to the guide 416 of FIGS. 1-15 and the guide 416' of FIGS. 16-24 and therefore, structures of FIGS. 30-39 that are the same as or similar to those described with reference to FIGS. 1-15 and/or 16-24 have the same reference numbers with the addition of a "prime" mark. Description of common elements and operation similar to those in the previously described first embodiment will not be repeated with respect to the second embodiment.

FIGS. 30-39 depict fourth through eighth configurations of a guide 416' of the second embodiment of the present invention and combines features of the previous three configurations of the second embodiment, as well as some features of the guide 416 of the first embodiment. The guides 416' of FIGS. 30-39 each have a relatively complex base structure with a lower base surface 520' which is spread across a plurality of extended portions 2278. The various segments of the lower base surface 520' concurrently contact at least a portion of a primary patient tissue area 108' and at least a portion of a secondary patient tissue area 110'. A plurality of guiding bosses 428' are provided to the guides 416' of FIGS. 30-39, including at least one "outboard" guiding boss located on an extended portion 2278 of the base body 424' to place landmarks 114' in the secondary patient tissue area 110' and a guiding boss located on a central portion 2280 of the base body to place a landmark 114' in the primary patient tissue area 108'.

The guiding boss 428' located on the central portion 2280 of the base body 424' in the guides 416' of FIGS. 30-39 is noticeably larger than the other guiding boss(es), and may serve several functions for the guides 416'. The guiding boss 428' located on the central portion 2280 of the base body 424' may guide a landmark 1114 through a guiding bore 430' thereof; may guide a rasp, drill, or other tissue modification tool (not shown) therethrough, optionally providing a "stop" function to limit insertion of the tissue modification tool into the underlying patient tissue; and/or may serve as a handling boss for user manipulation by hand and/or with a handling tool.

The guides 416' of FIGS. 30-39 differ from each other mainly in the number and configuration(s) of extended portions 2278, which may be chosen to aid in stability, positive location, or any other characteristic/property of the guide with respect to the patient tissue area(s) 108' and/or 110'. As with all embodiments of the present invention, any extended portions 2278 present might include at least a portion of the lower base surface 520' or another patient-specific feature, or might be generic in structure. In cases where an extended portion 2278 is generic in structure, the location and/or dimensions of the extended portion may have patient-specific aspects in order to provide some locating function or assistance to the user. The extended portions 2278 shown in FIGS. 30-39 have locations, configurations, numbers, and are otherwise depicted in arrangements which help illustrate examples of guides 416' for various use environments of the present invention. The depicted guides 416' are not limiting as to the extended portions or any other properties of guides (not shown) for particular use environments of the present invention, which can be provided by one of ordinary skill of the art in a particular situation.

In FIGS. 30-31, three extended portions 2278 have segments of the lower base surface 520' which contact different portions of the secondary patient tissue area 110' (e.g., an acetabular rim) while a "central" portion of the lower base surface 520', located on or near the central portion 2280 of the base body 424', contacts the primary patient tissue area 108'.

In FIGS. 32-33, three extended portions 2278 have segments of the lower base surface 520' which contact different portions of the secondary patient tissue area 110' (e.g., an acetabular rim) while a "central" portion of the lower base surface 520', located on or near the central portion 2280 of the base body 424', contacts the primary patient tissue area 108'.

Figure 34:
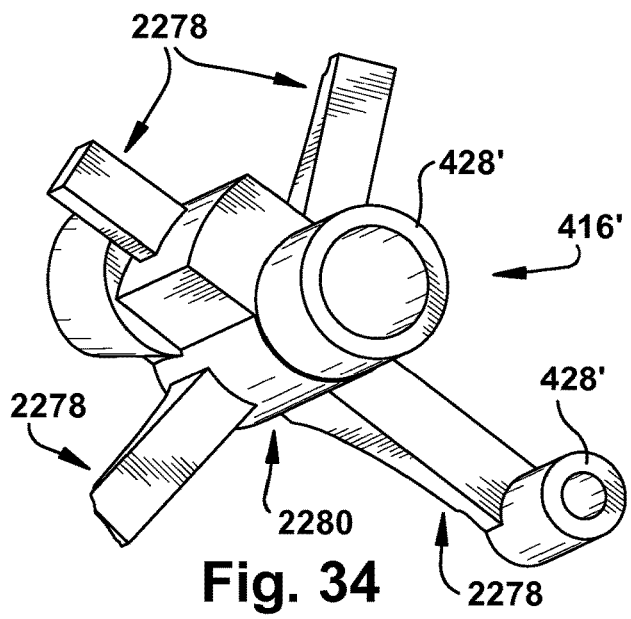
FIG. 34 is a perspective top view of the embodiment of FIG. 17 in a sixth configuration.
Figure 35:
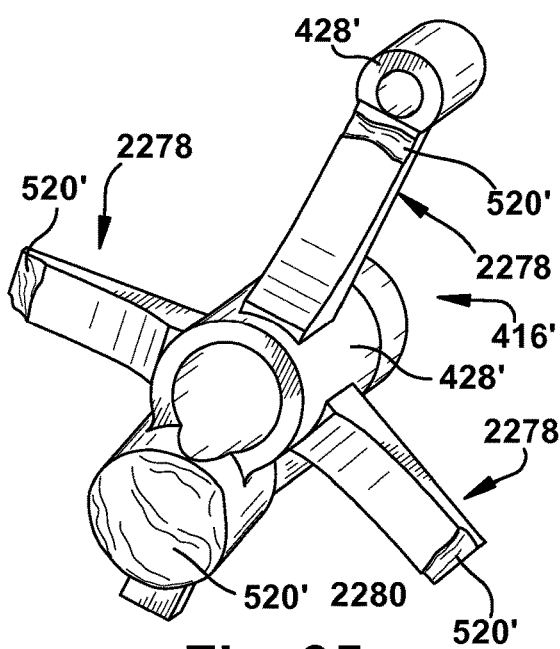
FIG. 35 is a perspective bottom view of the embodiment of FIG. 34.

In FIGS. 34-35, four extended portions 2278 have segments of the lower base surface 520' which contact different portions of the secondary patient tissue area 110' (e.g., an acetabular rim) while a "central" portion of the lower base surface 520', located on or near the central portion 2280 of the base body 424', contacts the primary patient tissue area 108'.

Figure 36:
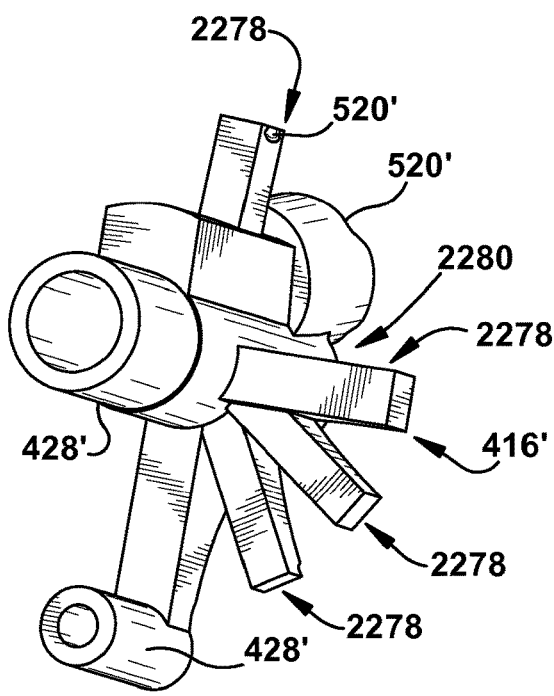
FIG. 36 is a perspective top view of the embodiment of FIG. 17 in a seventh configuration.
Figure 37:
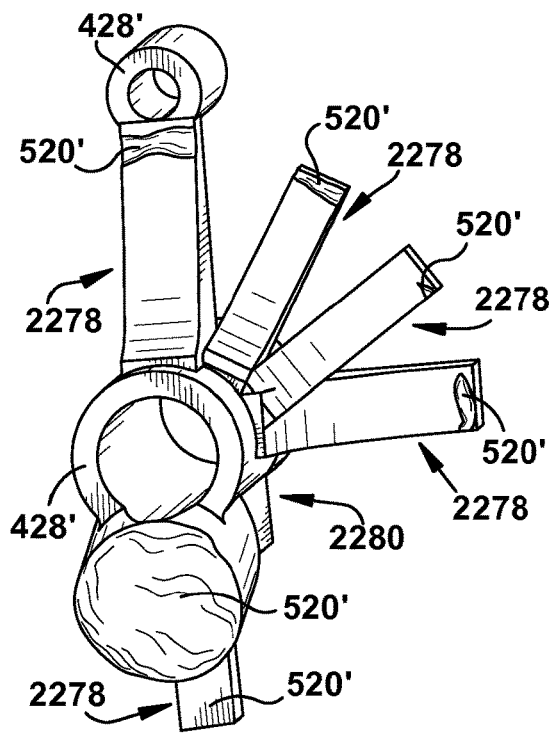
FIG. 37 is a perspective bottom view of the embodiment of FIG. 36.

In FIGS. 36-37, five extended portions 2278 have segments of the lower base surface 520' which contact different portions of the secondary patient tissue area 110' (e.g., an acetabular rim) while a "central" portion of the lower base surface 520', located on or near the central portion 2280 of the base body 424', contacts the primary patient tissue area 108'.

Figure 38:
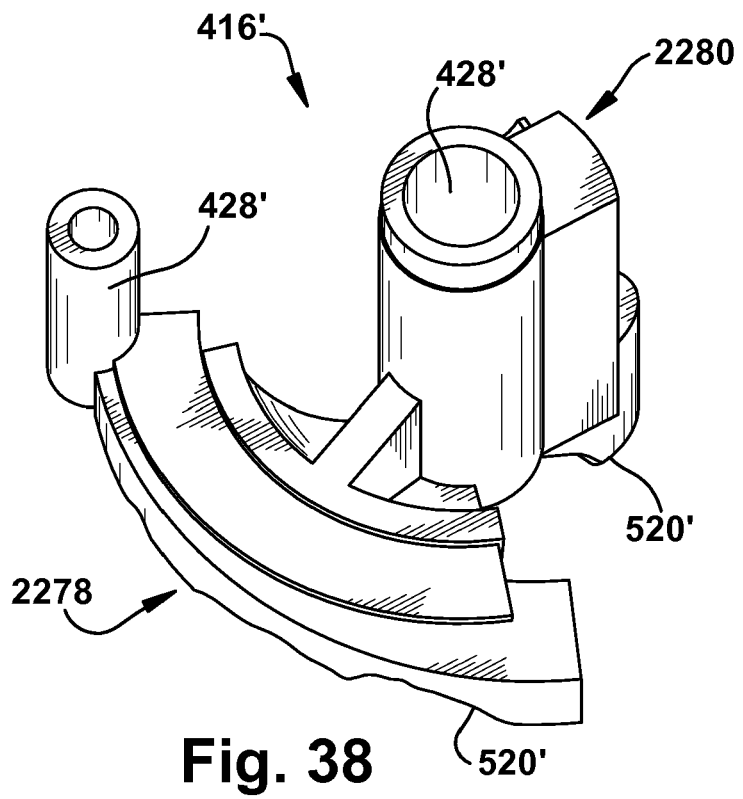
FIG. 38 is a perspective top view of the embodiment of FIG. 17 in a eighth configuration.
Figure 39:
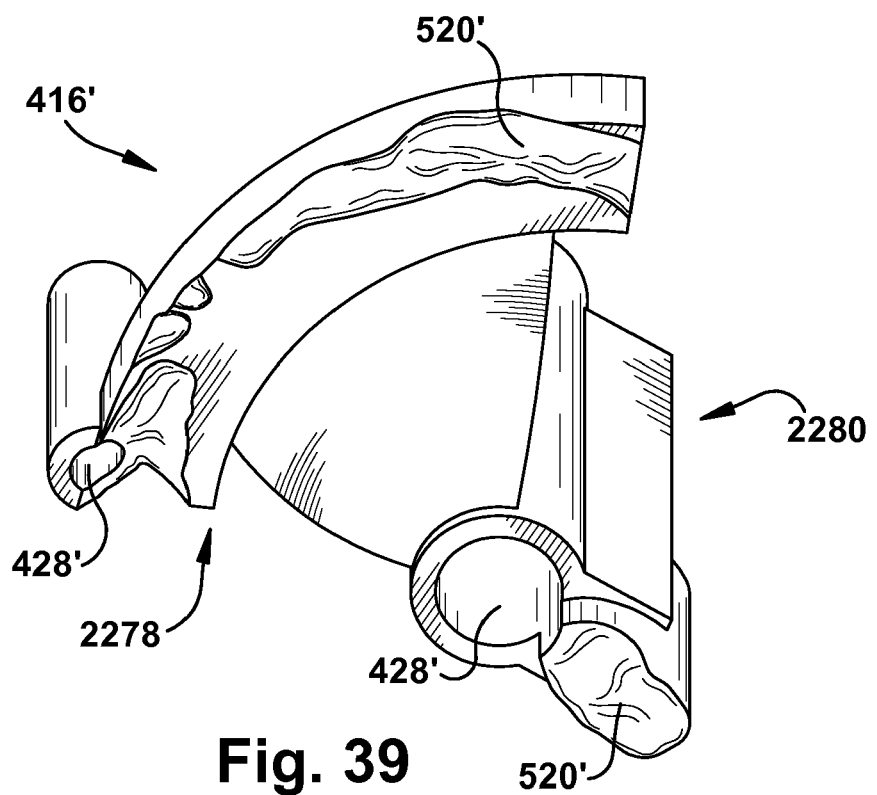
FIG. 39 is a perspective bottom view of the embodiment of FIG. 38.

In FIGS. 38-39, a single extended portion 2278 has an elongated segment of the lower base surface 520' which contacts at least a portion of the secondary patient tissue area 110' (e.g., an acetabular rim) while a "central" portion of the lower base surface 520', located on or near the central portion 2280 of the base body 424', contacts the primary patient tissue area 108'. It is contemplated that a plurality of slightly different guides 416 may be prepared for a particular surgical procedure, to allow desired landmark 114 placement regardless of intraoperative complications. For example, because the user will not necessarily be able to clear away surrounding patient tissue in situ as preoperatively planned, several guides 416 based upon differently sized, shaped, and/or oriented guide blanks 940 may be provided. Though each of these alternate guides 416 may be configured for placement of landmarks 114 in the same positions, the base bodies 424 may mate with different amounts and/or locations of the primary and/or secondary patient tissue areas 108 and 110. The user can then select one guide 416 from a range of alternates available, depending upon how much of the primary and/or secondary patient tissue area 108 and 110 was actually able to be substantially prepared for mating with the guide 416. As a variation of this option, a range of guides 416 embodying different landmark 114 placement schemes could be provided, with the user choosing one of the range of guides 416 once the true condition of the patient tissue can be seen during the surgical procedure. In this latter situation, a range of surgical plans are made preoperatively and the user chooses one of those plans for proceeding after the surgical procedure is underway.

An prosthetic implant is used as an example herein. However, it is contemplated that the disclosed guide 416 may be used additionally or alternatively with an instrument, such as that disclosed in co-pending U.S. patent application Ser. No. 13/282,528, filed Oct. 27, 2011, titled "System and Method for Assisting with Arrangement of a Stock Instrument with Respect to a Patient Tissue" and claiming priority to U.S. Provisional Patent Application No. 61/408,376, filed Oct. 29, 2010 and titled "System and Method for Assisting with Arrangement of a Stock Instrument with Respect to a Patient Tissue", the entire contents of both of which are incorporated herein by reference.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the guides 416 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. An adhesive (such as, but not limited to, bone cement) could be used in conjunction with the system and method described herein. The guide 416 may include a plurality of structures cooperatively forming the base body and temporarily or permanently attached together in such a manner as to permit relative motion (e.g., pivoting, sliding, or any other motion) therebetween. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

The invention claimed is:

1. A method of associating a plurality of landmarks with a patient tissue, each landmark being associated with the patient tissue in a predetermined marking location and/or a predetermined marking trajectory, the patient tissue including a primary patient tissue area adapted to directly receive an implant and an anatomically differentiated bordering secondary patient tissue area, the method comprising:
   obtaining a landmark guide having a base at least partially customized responsive to preoperative imaging of the patient tissue, the base having an upper base surface and a lower base surface opposite the upper base surface, the lower base surface contoured to mate with the primary patient tissue area, the portion of the lower base surface and the primary patient tissue area matching to achieve a preselected relative orientation;
   mating the base of the landmark guide with the primary patient tissue area in a preselected relative orientation;
   fixing a first landmark to the primary patient tissue area in the predetermined marking location and/or the predetermined marking trajectory while the base of the landmark guide is mated to the primary patient tissue area;
   fixing a guidewire pin to the secondary patient tissue area in the predetermined marking location and/or the predetermined marking trajectory while the base of the landmark guide is mated to the primary patient tissue area; and
   removing the landmark guide from mating engagement with the primary patient tissue area while the first landmark and guidewire pin remain fixed in the patient tissue.

2. The method of claim 1, wherein:
   the portion of the lower base surface and the primary patient tissue area are configured to achieve the preselected orientation between the portion of the lower base surface and the primary patient tissue area; and
   mating the base of the landmark guide with the primary patient tissue area includes concurrently mating the base of the landmark guide with the secondary patient tissue area in the preselected relative orientation.

3. The method of claim 1, wherein mating the base of the landmark guide with the primary patient tissue area includes using a base having a lower base surface contoured to mate with both the primary and secondary patient tissue areas in the preselected relative orientation, the lower base surface being spaced apart from the upper base surface by a base body; and
   wherein fixing a first landmark to the primary patient tissue area includes:
   guiding the placement of the first landmark through at least one base aperture extending between the upper and lower base surfaces through the base body, and through at least one guiding boss protruding from the base, the at least one guiding boss having a guiding bore extending therethrough, the at least one guiding bore extending collinearly with the at least one base aperture to permit insertion of the first landmark therethrough, and cooperatively defining at least one of the predetermined marking location and the predetermined marking trajectory for the first landmark with each guiding bore and corresponding base aperture.

4. The method of claim 1, wherein mating the base of the landmark guide with the primary patient tissue area includes using a base having a lower base surface contoured to mate with the primary patient tissue area in the preselected relative orientation, the lower base surface being spaced apart from the upper base surface by a base body; and
   wherein fixing a guidewire pin to the secondary patient tissue area includes:
   guiding the placement of the guidewire pin through an arm guide aperture in at least one of the predetermined marking location and/or the predetermined marking trajectory, the predetermined marking location being in the secondary patient tissue area, the arm guide aperture laterally spaced and connected to at least one spacing arm, a stem having longitudinally separated first and second stem ends, the first stem end being attached directly to the base and the stem extending upward from the base, the at least one spacing arm attached directly to the second stem end, the at least one spacing arm being longitudinally spaced from the base.

5. The method of claim 4, wherein:
   the landmark guide comprises a base guide aperture; and
   fixing a first landmark to the primary patient tissue area includes guiding the placement of a landmark inserted at least partially through the base guide aperture in the base in at least one of the predetermined marking location and/or the predetermined marking trajectory, the predetermined marking location being in the primary patient tissue area.

6. The method of claim 1, wherein:
   the portion of the lower base surface and the primary patient tissue area are configured to achieve the preselected orientation guided by the primary patient tissue area; and
   mating the base of the landmark guide with the primary patient tissue area comprises manipulating the base by at least one handling boss protruding from the base.

7. The method of claim 1, wherein fixing the first landmark to the primary patient tissue area in the predetermined marking location and/or the predetermined marking trajectory comprises fixing the first landmark in a planned center of a stem of an implant to be positioned on the bone.

8. The method of claim 1, wherein fixing the first landmark to the primary patient tissue area comprises fixing the first landmark in the glenoid fossa.

9. The method of claim 8, wherein:
fixing the guidewire pin to the secondary patient tissue area comprises:
  fixing the guidewire pin to a portion of a scapula outside of the glenoid fossa; and
  clamping the landmark guide onto opposite sides of a rim of the glenoid in the secondary patient tissue area.

10. The method according to claim 1, wherein:
fixing the first landmark to the primary patient tissue area comprises making a hole in the primary patient tissue area; and
making the hole in the primary patient tissue area comprises making the hole in a position corresponding to a planned center of a stem of an implant to be positioned on the bone.

11. The method according to claim 1, further comprising:
altering the patient tissue at the primary patient tissue area at a location that is a predetermined distance from the guidewire pin based on the preoperative imaging of the patient tissue; and
inserting an implant onto the primary patient tissue area.

12. The method according to claim 11, wherein:
fixing the first landmark to the primary patient tissue area further comprises inserting a guide pin through the first aperture in the landmark guide;
fixing the guidewire pin to the secondary patient tissue area further comprises inserting the guidewire pin through a second aperture in the landmark guide; and
obtaining a landmark guide further comprises obtaining a landmark guide comprising:
  a stem extending upward from the base, and
  at least one spacing arm extending from the stem, each spacing arm defining a corresponding aperture; and
  wherein at least one of the spacing arms defines the second aperture and is configured to guide the guidewire pin to the secondary patient tissue area in the predetermined marking location and/or the predetermined marking trajectory.

13. The method according to claim 1, wherein:
the lower base surface is contoured to have a unique complimentary engagement with the primary patient tissue area; and
the portion of the lower base surface is configured to match with the primary patient tissue to fix the landmark guide in the preselected relative orientation with respect to the primary patient tissue.

14. The method according to claim 1, wherein:
the landmark guide further comprises:
  a central portion defining a first guiding bore having a first aperture and a second aperture opposite the first aperture, the central portion configured to receive a tool via the first aperture and to guide the tool via the first guiding bore for placing a first landmark;
  at least one extended portion projecting away from the central portion, each of the at least one extended portion having a respective lower base surface contoured to mate with the patient tissue, and
  a guide portion distinct from the at least one extended portion and projecting away from the central portion, the guide portion having a second guiding bore spaced apart from the first guiding bore and configured for placing the guidewire pin;
at least a portion of a perimeter of the second aperture is offset from the lower base surface; and
the lower base surface of the landmark guide is configured to be mated with the primary patient tissue in a preselected relative orientation such that at least the portion of the perimeter of the second aperture of the first guiding bore is spaced from the primary patient tissue area while the landmark guide is mated to the primary tissue area.

15. The method according to claim 14, wherein the at least one extended portion comprises at least three extended portions each having respective lower base surfaces contoured to mate with the patient tissue, the respective lower base surfaces being customized as a function of the preoperative imaging of the patient tissue.

16. The method according to claim 14, wherein:
each of the extended portions comprises a respective bottom surface connecting the respective lower base surfaces of the extended portion to the central portion, each of the respective bottom surfaces being free of contouring to mate with the patient tissue; and
whereby the landmark guide is specific to a patient corresponding to the patient tissue.

17. The method according to claim 1, wherein:
the secondary patient tissue area comprises a rim that neighbors the primary patient tissue area; and
the lower base surface is contoured to mate solely with the primary patient tissue area.

18. The method according to claim 1, wherein:
the landmark guide defines a first guiding bore having a first aperture and a second aperture opposite the first aperture, the first guide bore configured to receive a tool via the first aperture and to guide the tool to the primary tissue area via the second aperture; and
the lower base surface of the landmark guide is configured to be mated with the primary patient tissue in a preselected relative orientation such that at least the portion of a perimeter of the second aperture is spaced from the primary patient tissue area while the landmark guide is mated to the primary tissue area in the preselected relative orientation.

19. The method according to claim 1, wherein:
the landmark guide further comprises:
  a central portion defining a first guiding bore having a first aperture and a second aperture opposite the first aperture, the central portion configured to receive a tool via the first aperture and to guide the tool via the first guiding bore for placing a first landmark; and
  at least one extended portion projecting away from the central portion, each of the at least one extended portion having a respective lower base surface contoured to mate with the patient tissue;
at least a portion of a perimeter of the second aperture is offset from the lower base surface; and
the landmark guide further comprises a guide portion distinct from the at least one extended portion and projecting away from the central portion of the landmark guide, the guide portion having a second guiding bore spaced apart from the first guiding bore, and the guide portion configured for placing the guidewire pin.

20. The method according to claim 1, wherein:
the lower base surface of the landmark guide includes:
  a first portion contoured to mate with the primary patient tissue area; and
  a second portion contoured to make with the secondary patient tissue area; and the lower base surface includes a continuous contoured surface from the first portion to the second portion.

* * * * *